(12) United States Patent
Fenech

(10) Patent No.: US 11,547,507 B2
(45) Date of Patent: Jan. 10, 2023

(54) VARIABLE-LENGTH GUIDE APPARATUS FOR DELIVERY OF A FLEXIBLE INSTRUMENT AND METHODS OF USE

(71) Applicant: INTUITIVE SURGICAL OPERATIONS, INC., Sunnyvale, CA (US)

(72) Inventor: Carolyn M. Fenech, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 327 days.

(21) Appl. No.: 16/867,393

(22) Filed: May 5, 2020

(65) Prior Publication Data

US 2020/0261175 A1    Aug. 20, 2020

Related U.S. Application Data

(63) Continuation of application No. 15/717,089, filed on Sep. 27, 2017, now Pat. No. 10,682,192.
(Continued)

(51) Int. Cl.
*A61B 5/00* (2006.01)
*A61B 34/00* (2016.01)
(Continued)

(52) U.S. Cl.
CPC .......... *A61B 34/70* (2016.02); *A61B 1/00154* (2013.01); *A61B 34/35* (2016.02);
(Continued)

(58) Field of Classification Search
CPC ..... A61B 34/70; A61B 1/00154; A61B 34/35; A61B 34/37; A61B 34/71; A61B 90/06;
(Continued)

(56) References Cited

U.S. PATENT DOCUMENTS

| | | | |
|---|---|---|---|
| 5,749,828 A | * | 5/1998 | Solomon .............. A61B 1/0055 600/141 |
| 6,331,181 B1 | | 12/2001 | Tierney et al. |

(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — May A Abouelela
(74) *Attorney, Agent, or Firm* — Haynes and Boone, LLP

(57) ABSTRACT

An apparatus for guiding an elongated flexible instrument, includes a first plurality of linkages forming a first side of a channel of a variable-length support assembly, a second plurality of linkages forming a second side of the channel, opposite the first side, a third plurality of linkages disposed between the first and second plurality of linkages and forming a third side of the channel, and a fourth plurality of linkages disposed between the first and second plurality of linkages and forming a fourth side of the channel, opposite the third side. Each of the first, second, third, and fourth pluralities of linkages are separable from each other to transition the variable-length support assembly from an elongated configuration to a compact configuration.

20 Claims, 35 Drawing Sheets

Related U.S. Application Data

(60) Provisional application No. 62/402,654, filed on Sep. 30, 2016.

(51) Int. Cl.

| | | |
|---|---|---|
| *A61B 34/35* | (2016.01) | |
| *A61B 34/37* | (2016.01) | |
| *A61B 90/00* | (2016.01) | |
| *A61B 1/00* | (2006.01) | |
| *A61B 1/005* | (2006.01) | |
| *A61B 10/06* | (2006.01) | |
| *A61B 1/05* | (2006.01) | |
| *A61B 34/30* | (2016.01) | |

(52) U.S. Cl.
CPC ............. *A61B 34/37* (2016.02); *A61B 34/71* (2016.02); *A61B 90/06* (2016.02); *A61B 1/0051* (2013.01); *A61B 1/05* (2013.01); *A61B 10/06* (2013.01); *A61B 34/74* (2016.02); *A61B 2034/301* (2016.02); *A61B 2034/306* (2016.02); *A61B 2090/064* (2016.02); *A61B 2090/066* (2016.02)

(58) Field of Classification Search
CPC ......... A61B 1/0051; A61B 1/05; A61B 10/06; A61B 34/74; A61B 2034/301; A61B 2034/306; A61B 2090/064; A61B 2090/066
See application file for complete search history.

(56) References Cited

U.S. PATENT DOCUMENTS

| | | | |
|---|---|---|---|
| 6,380,732 B1 | 4/2002 | Gilboa | |
| 6,389,187 B1 | 5/2002 | Greenaway et al. | |
| 6,491,701 B2 | 12/2002 | Tierney et al. | |
| 7,316,681 B2 | 1/2008 | Madhani et al. | |
| 7,634,874 B2 * | 12/2009 | Lucas | E04C 3/005 52/645 |
| 7,682,319 B2 * | 3/2010 | Martin | A61B 50/30 604/165.01 |
| 7,772,541 B2 | 8/2010 | Froggatt et al. | |
| 8,348,834 B2 * | 1/2013 | Bakos | A61B 17/3417 600/141 |
| 8,672,880 B2 | 3/2014 | Cohen et al. | |
| 8,758,270 B2 * | 6/2014 | Ryan | F16D 3/52 600/585 |
| 8,900,131 B2 | 12/2014 | Chopra et al. | |
| 8,961,533 B2 | 2/2015 | Stahler et al. | |
| 9,113,783 B2 * | 8/2015 | Suehara | A61B 1/008 |
| 9,259,274 B2 | 2/2016 | Prisco | |
| 9,452,276 B2 | 9/2016 | Duindam et al. | |
| 10,434,288 B2 * | 10/2019 | Hansen | A61M 25/09 |
| 2003/0233058 A1 * | 12/2003 | Ewers | A61B 1/00105 600/585 |
| 2004/0254450 A1 * | 12/2004 | Griffin | A61M 25/0127 600/411 |
| 2006/0013523 A1 | 1/2006 | Childers et al. | |
| 2006/0178562 A1 * | 8/2006 | Saadat | A61B 1/0055 600/142 |
| 2006/0200000 A1 * | 9/2006 | Sato | A61B 1/0057 600/146 |
| 2007/0135683 A1 * | 6/2007 | Bob | A61B 1/00082 600/114 |
| 2007/0156019 A1 * | 7/2007 | Larkin | A61B 1/009 600/104 |
| 2010/0160735 A1 * | 6/2010 | Bakos | A61B 17/3417 600/141 |
| 2011/0065993 A1 * | 3/2011 | Belson | A61B 1/31 600/141 |
| 2011/0251519 A1 * | 10/2011 | Romoscanu | A61M 25/0053 600/585 |
| 2014/0155702 A1 * | 6/2014 | Tilson | A61B 1/07 600/300 |
| 2014/0166718 A1 * | 6/2014 | Swayze | A61B 17/1155 227/175.1 |
| 2014/0243592 A1 * | 8/2014 | Kato | A61B 17/00234 600/141 |
| 2014/0378767 A1 * | 12/2014 | Lee | A61B 1/005 600/141 |
| 2015/0320295 A1 * | 11/2015 | Belson | H01L 41/0926 600/141 |
| 2016/0135663 A1 * | 5/2016 | Isoda | A61B 1/0057 600/149 |
| 2018/0092701 A1 | 4/2018 | Fenech | |
| 2018/0214138 A9 * | 8/2018 | Prisco | A61B 17/00 |

* cited by examiner

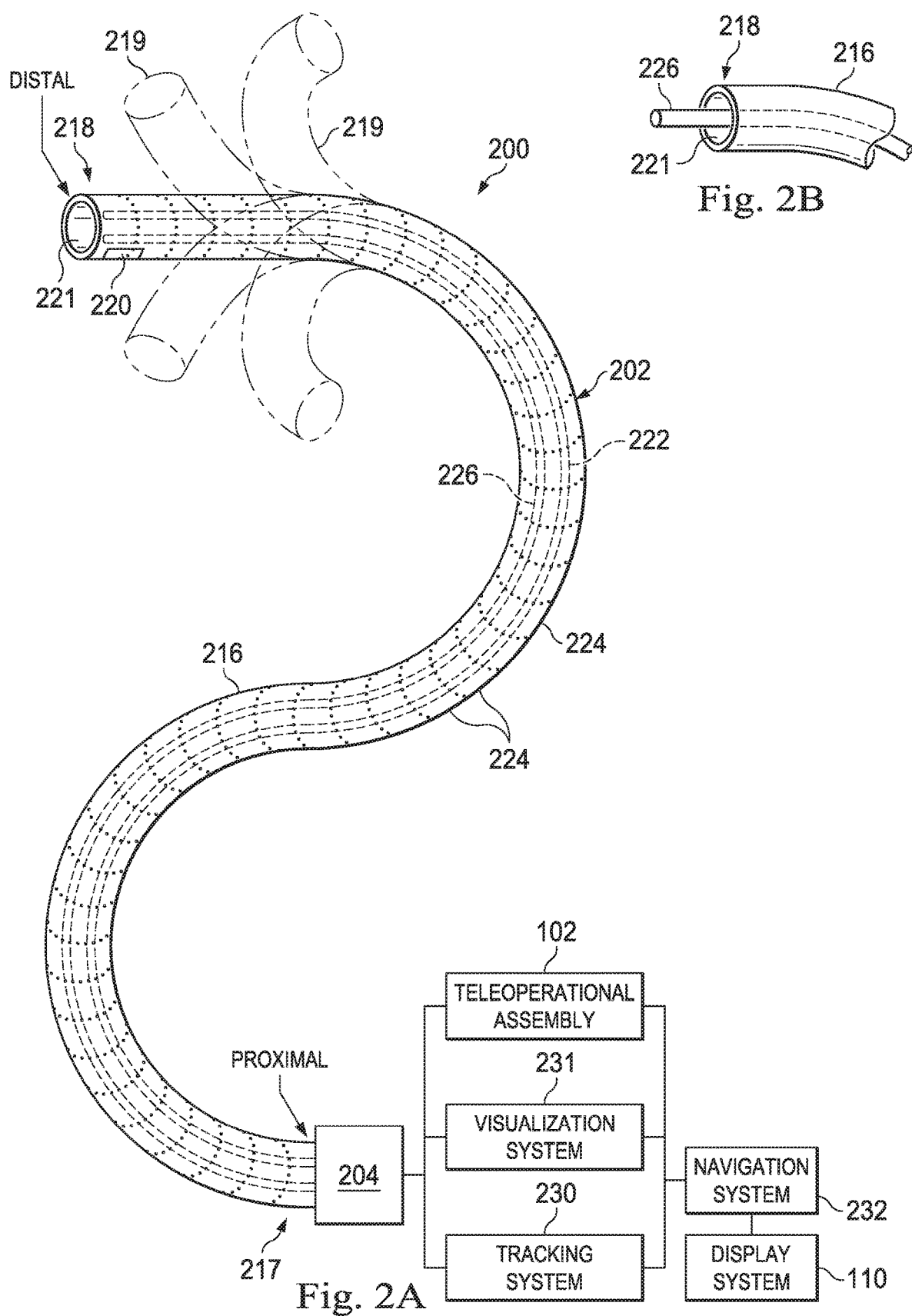

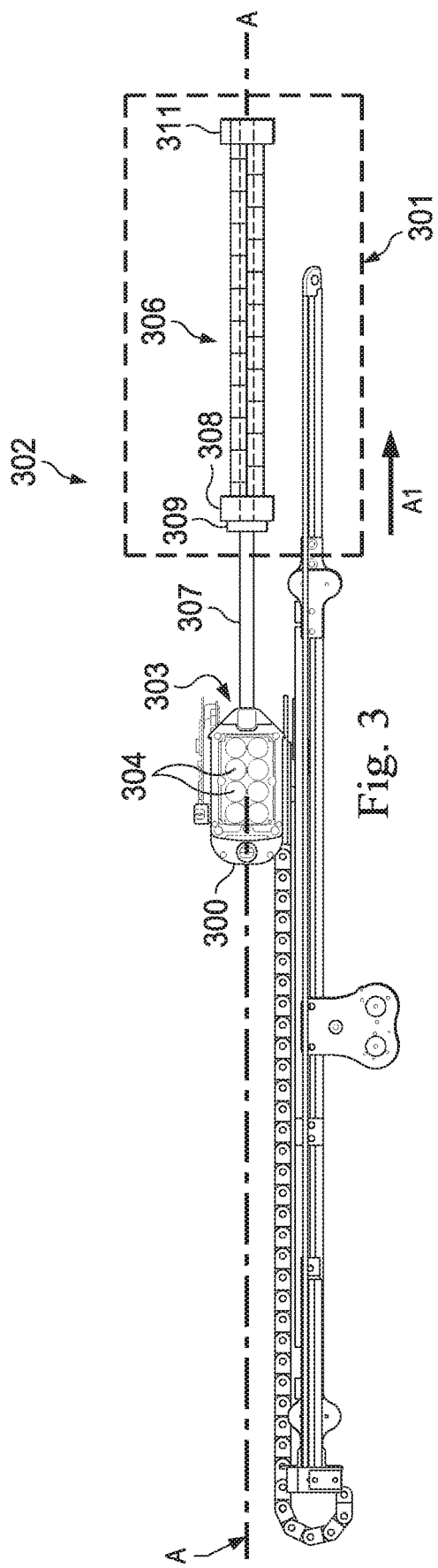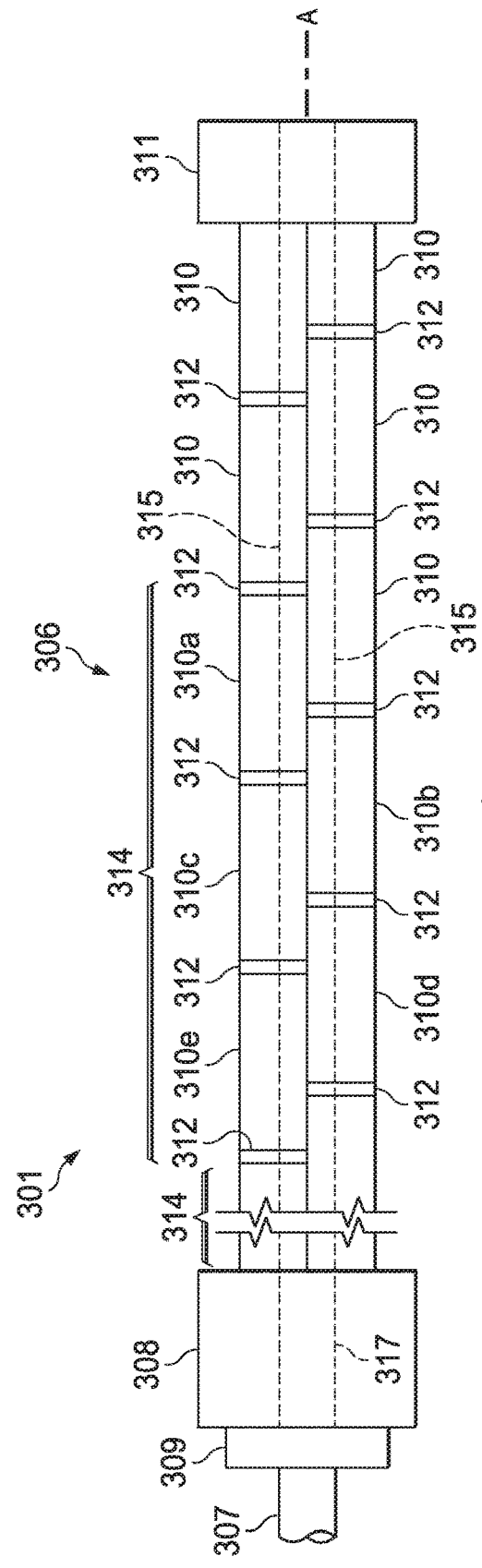

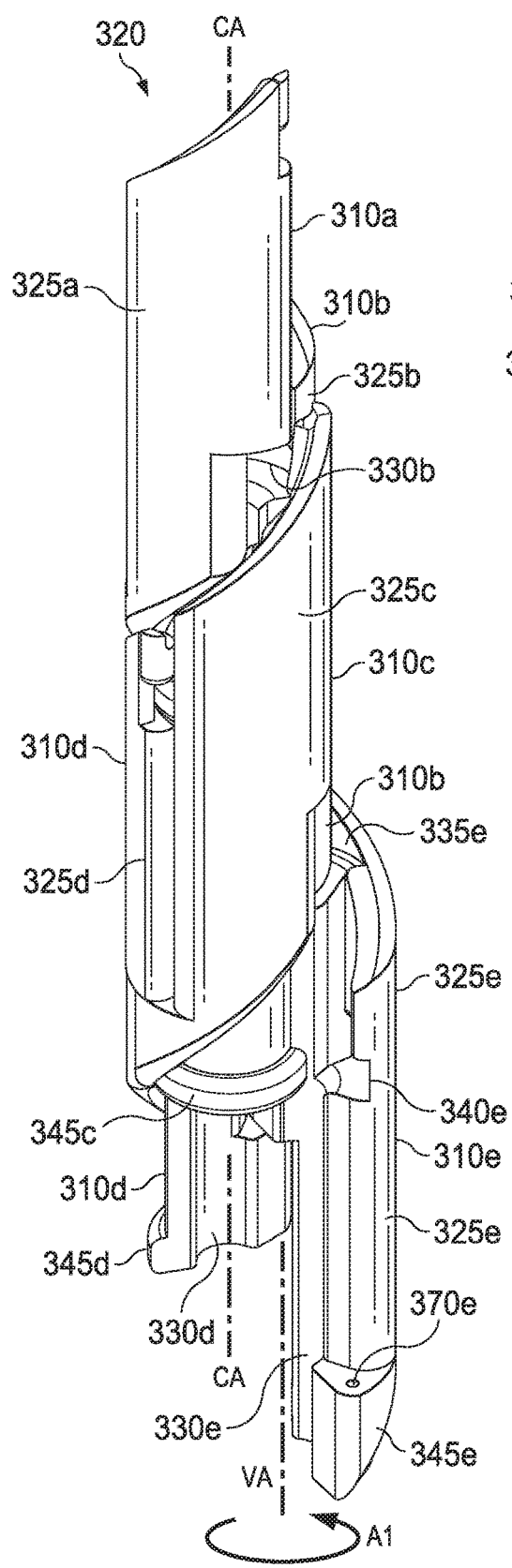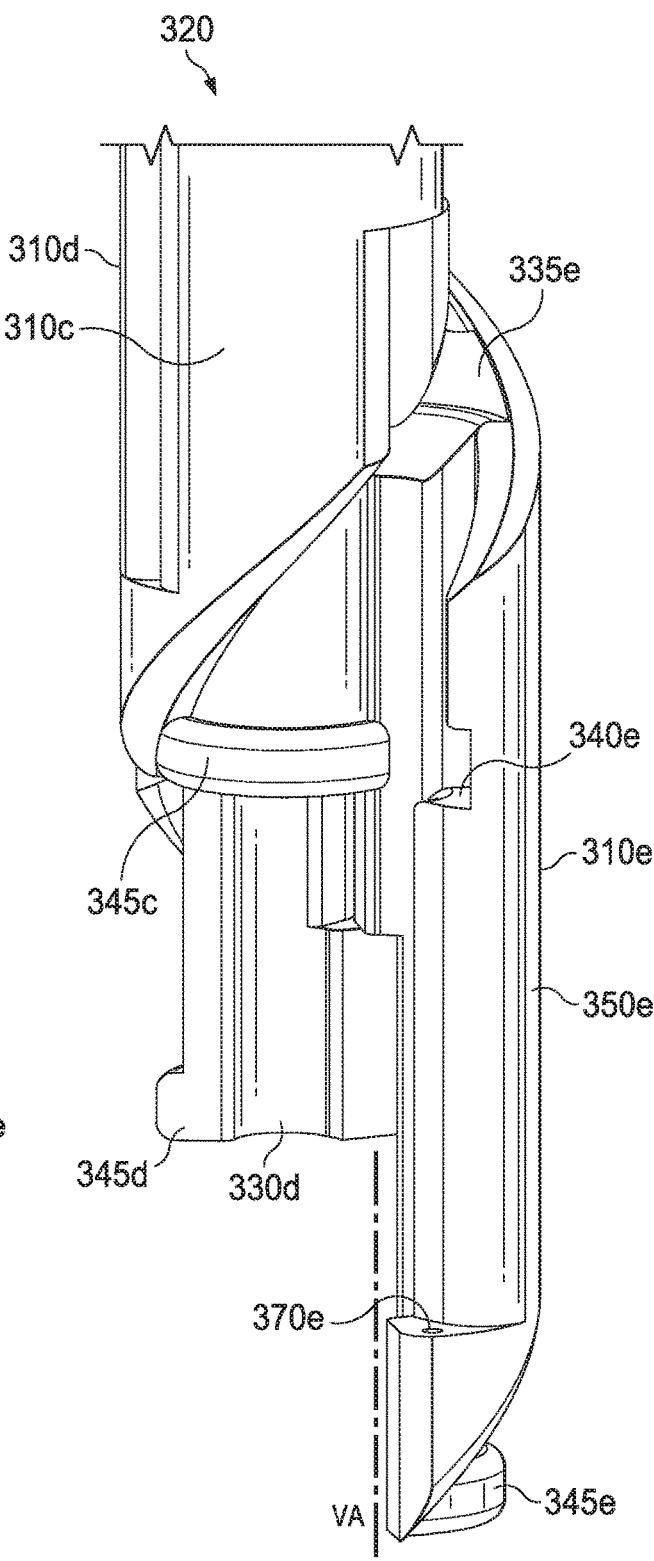
Fig. 5A
Fig. 5B

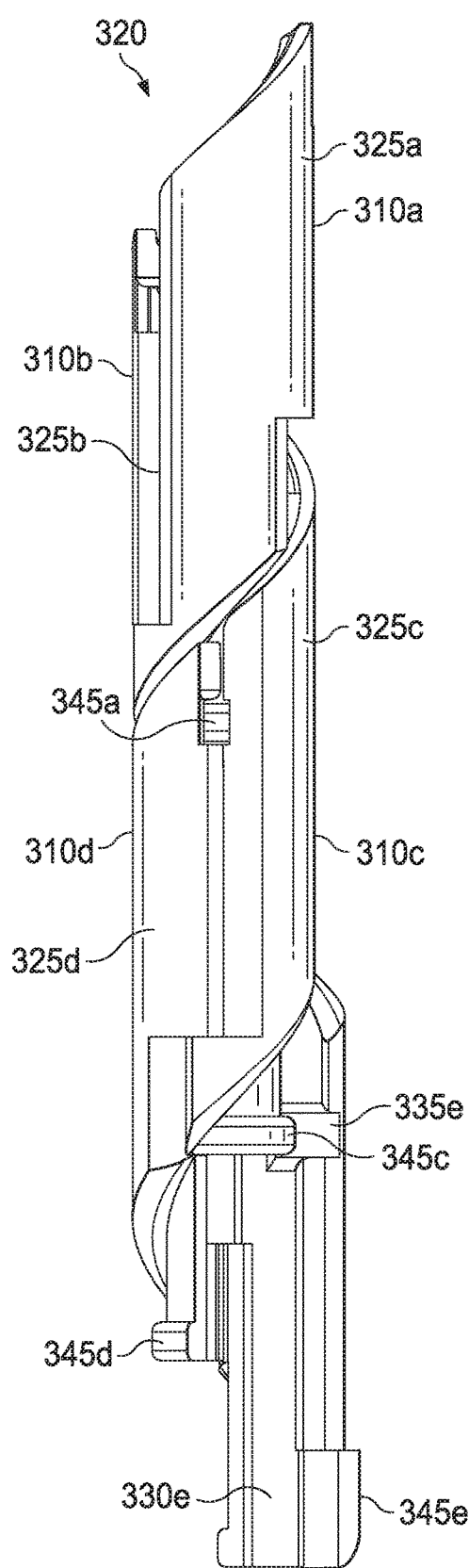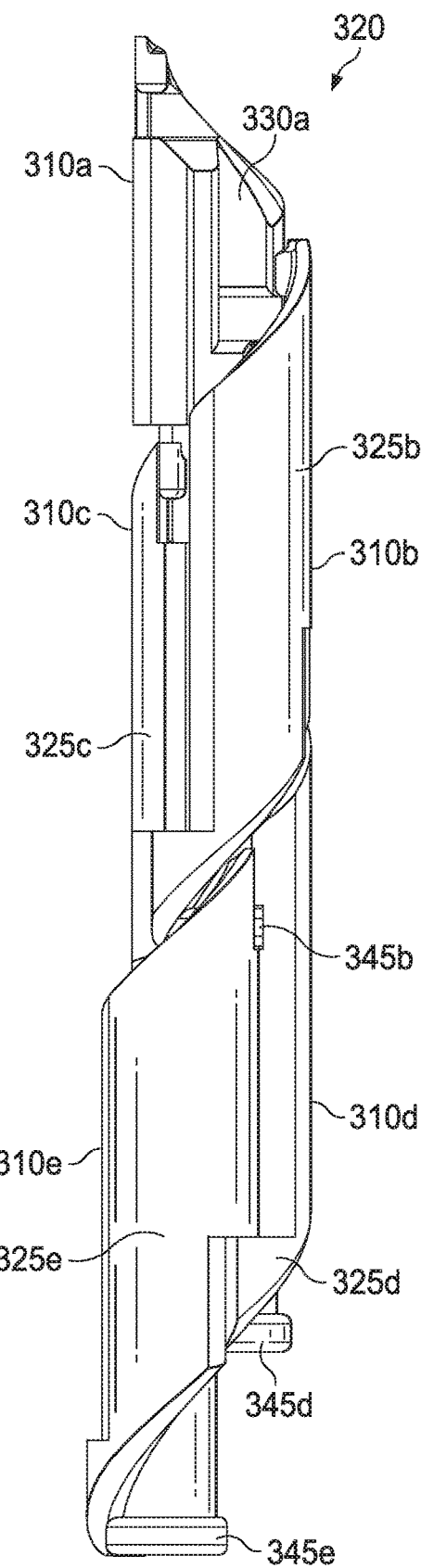
Fig. 6A
Fig. 6B

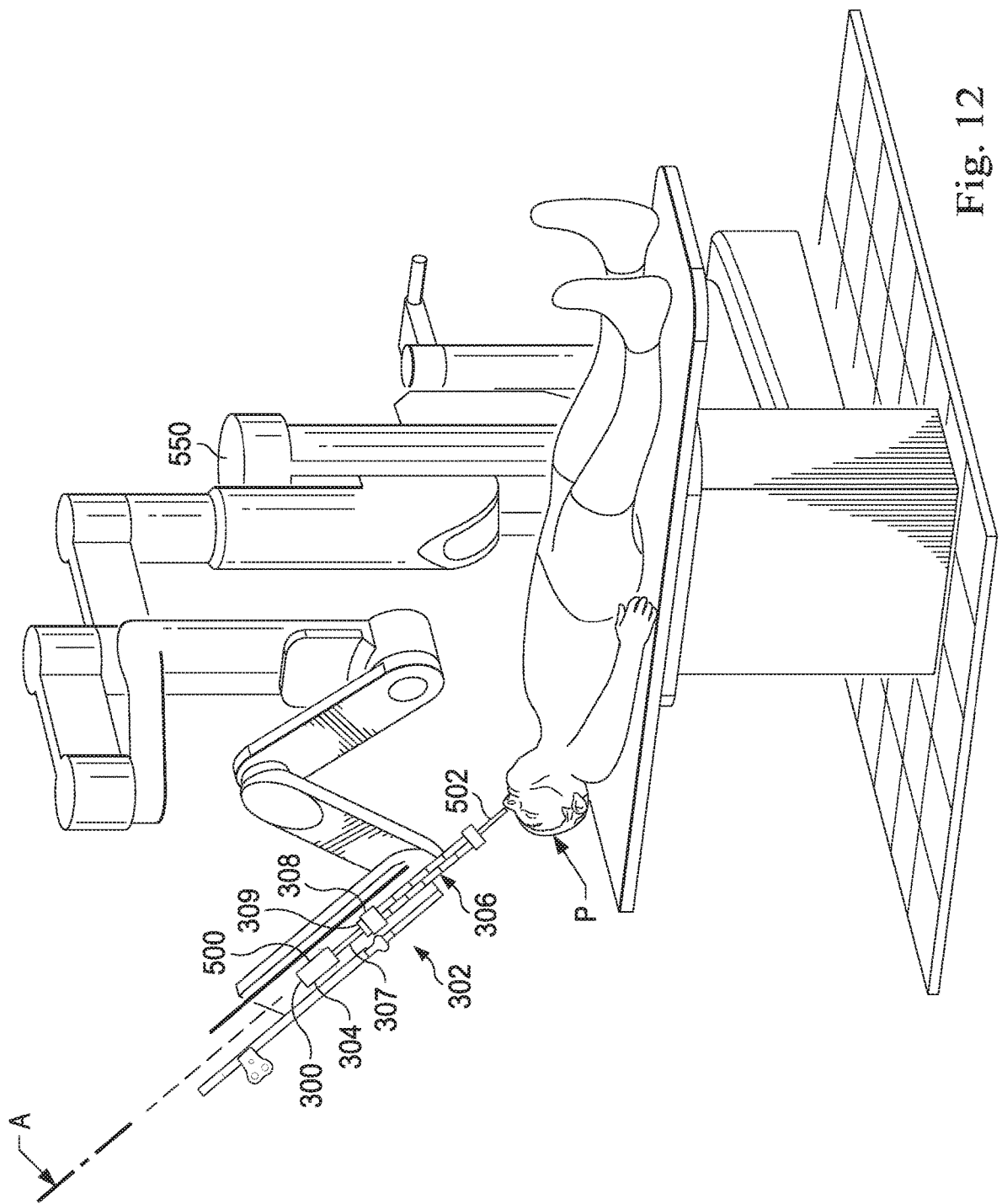

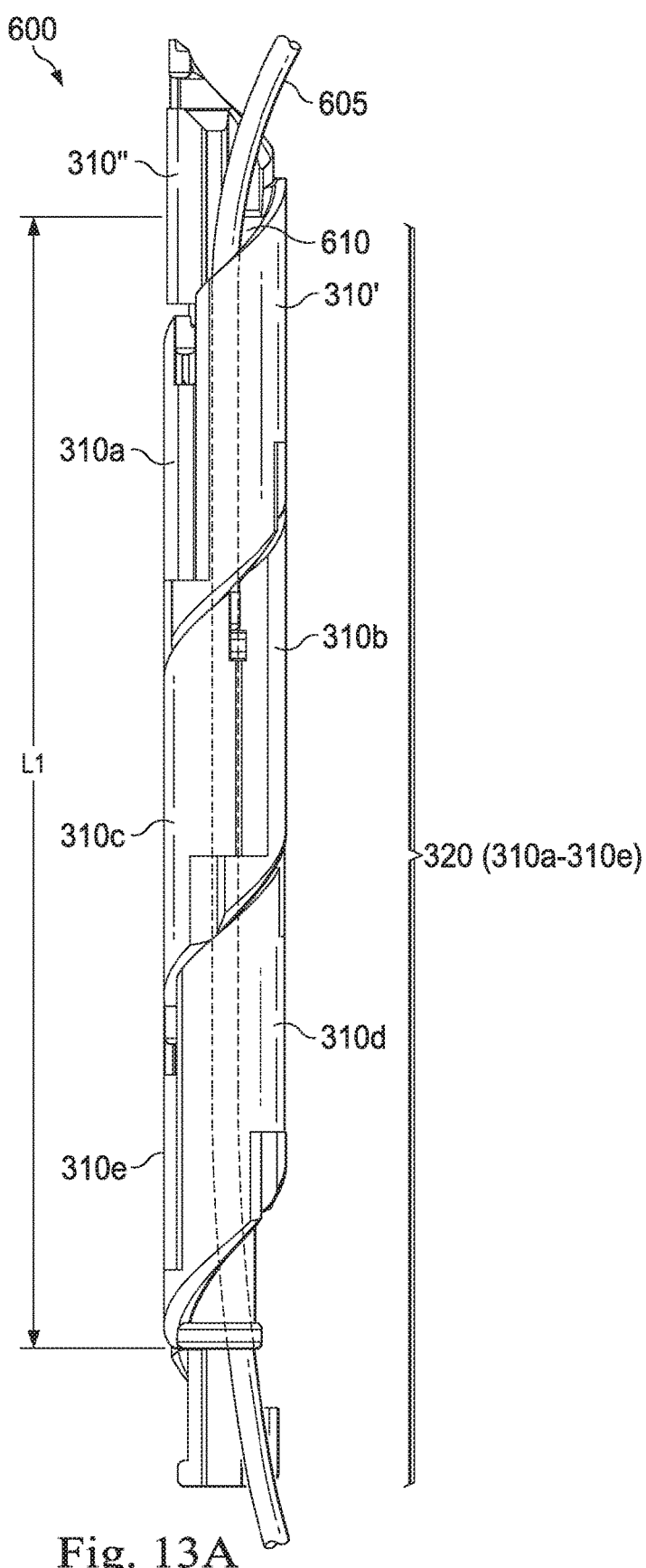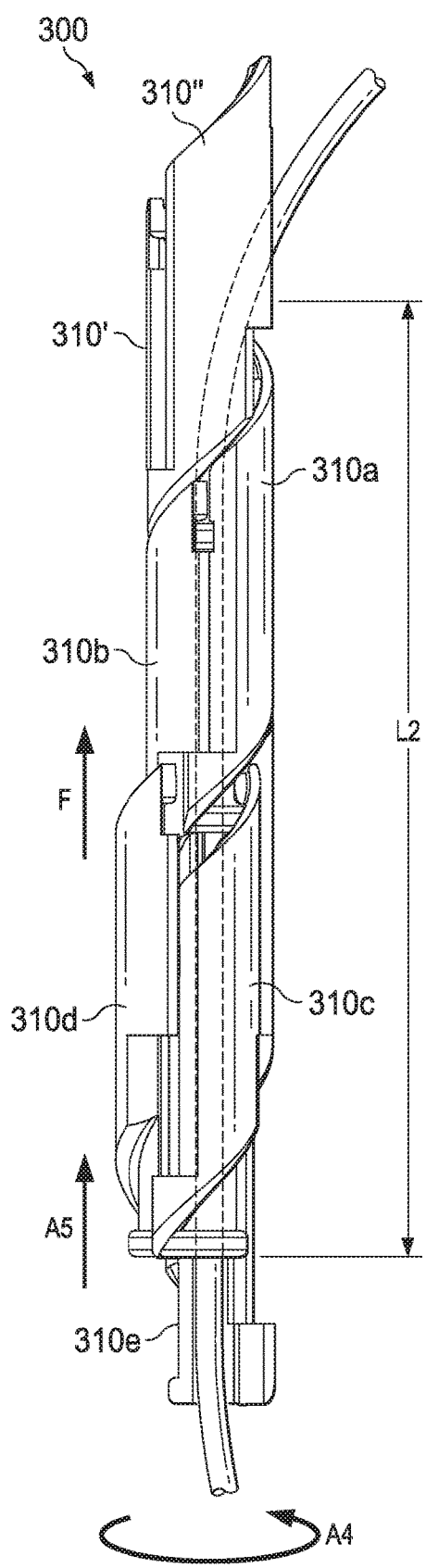
Fig. 13A
Fig. 13B

VARIABLE-LENGTH GUIDE APPARATUS FOR DELIVERY OF A FLEXIBLE INSTRUMENT AND METHODS OF USE

RELATED APPLICATIONS

This patent application is a continuation of U.S. patent application Ser. No. 15/717,089 filed Sep. 27, 2017, which claims priority to and the benefit of the filing date of U.S. Provisional Patent Application 62/402,654, entitled "Variable-Length Guide Apparatus For Delivery Of A Flexible Instrument and Methods of Use," filed Sep. 30, 2016, both of which are incorporated by reference herein in their entirety.

FIELD

The present disclosure is directed to systems and methods for navigating a patient anatomy to conduct a minimally invasive procedure, and more particularly to apparatus and methods for guiding and supporting delivery of a flexible interventional instrument into a patient anatomy.

BACKGROUND

Minimally invasive medical techniques are intended to reduce the amount of tissue that is damaged during interventional procedures, thereby reducing patient recovery time, discomfort, and harmful side effects. Such minimally invasive techniques may be performed through natural orifices in a patient anatomy or through one or more surgical incisions. Physicians may insert minimally invasive medical instruments (including surgical, diagnostic, therapeutic, or biopsy instruments) through these natural orifices or incisions to reach a target tissue location. One such minimally invasive technique is to use a flexible and/or steerable elongate device, such as a flexible catheter, that can be inserted into anatomic passageways and navigated toward a region of interest within the patient anatomy. To reach the target tissue location, a minimally invasive interventional instrument may navigate natural or surgically created passageways in anatomical systems such as the lungs, the colon, the intestines, the kidneys, the heart, the circulatory system, or the like. Control of such an elongate device by medical personnel involves the management of several degrees of freedom including at least the management of insertion and retraction of the elongate device as well as steering of the device. In addition, different modes of operation may also be supported.

Teleoperational interventional systems may be used to insert the interventional instruments into the patient anatomy. Several interventional instruments are made of flexible material that allows for maneuverability through a patient's body. In existing systems, at least a portion of the interventional instrument extending between the patient and a teleoperational manipulator is unsupported which may cause the instrument to bend and buckle as it is inserted into the patient anatomy. Deformation of the instrument may damage internal components such as optical fiber shape sensors or endoscopic equipment.

Improved systems and methods are needed for guiding and supporting interventional instruments as they are inserted into a patient anatomy to prevent instrument deformation.

SUMMARY

The embodiments of the invention are summarized by the claims that follow the description.

In one embodiment, the present disclosure describes an apparatus for guiding an elongated flexible instrument, the apparatus comprising a variable-length support assembly. The variable-length support assembly includes a plurality of linkages connected in series along a longitudinal axis, and has a compact configuration and an expanded configuration. In one aspect, the variable-length support assembly is adapted to maintain a length of the elongated flexible instrument in a fixed configuration relative to the variable-length support assembly as the variable-length support assembly is moved along the longitudinal axis.

In one aspect, the variable-length support assembly includes a central lumen formed by the plurality of linkages, wherein the central channel is configured to receive the elongated flexible instrument.

In one aspect, at least two linkages of the plurality of linkages are connected in series by a hinge component. In one aspect, each linkage of the plurality of linkages is movable relative to an adjacent linkage about the hinge component.

In one aspect, each linkage of the plurality of linkages is configured for rotational movement about the hinge component relative to an adjacent linkage. In another aspect, each of the linkages is configured for linear translation about the hinge component relative to an adjacent linkage.

In one aspect, the apparatus further comprises a return assembly configured to receive at least one of the plurality of linkages to shorten the variable-length support assembly as the elongated flexible instrument is moved along the longitudinal axis.

In one aspect, the variable-length support assembly includes multiple strips of linkages connected in series that are interlocked along the longitudinal axis.

In another embodiment, the present disclosure describes a guiding apparatus comprising a variable-length support assembly that includes a plurality of linkages and a return assembly having a first central lumen. The variable-length support assembly extends along a longitudinal axis and has a second central lumen, a proximal end, and a distal end, in addition to an expanded configuration and a compact configuration. The return assembly is adjacent the proximal end of the variable-length support assembly. In one aspect, each linkage includes an inner surface, and each linkage is coupled to at least one adjacent linkage along the longitudinal axis with the inner surfaces of the adjacent linkages joined to form a continuous second central lumen through the variable-length support assembly. Advancement of the return assembly along the longitudinal axis separates the proximal end of the support assembly, directing individual linkages into the return assembly and causing the variable-length support assembly to assume the compact configuration.

In one aspect, the variable-length support assembly is adapted to maintain a length of the elongated flexible instrument in a fixed configuration relative to the variable-length support assembly as the return assembly is moved along the longitudinal axis.

In one aspect, directing individual linkages into the return assembly comprises rotating individual linkages away from away from the second central lumen and the longitudinal axis.

In another aspect, directing individual linkages into the return assembly comprises sliding individual linkages along the longitudinal axis.

In one aspect, each linkage includes a projection and a recess, wherein the projection of a first linkage of the plurality of linkages interlocks with the recess of a second linkage of the plurality of linkages when the variable-length support assembly assumes an expanded configuration.

In one aspect, the return assembly comprises a hollow spiral configured to receive a plurality of linkages.

In another embodiment, the present disclosure is directed to a method of guiding an interventional instrument, the method comprising providing a variable-length support assembly extending along a longitudinal axis and having a proximal end, a distal end and a first length, the support assembly including a plurality of linkages, with each linkage of the plurality of linkages interlocked with an adjacent linkage along the longitudinal axis to form a continuous central lumen through the variable-length support assembly. The method further comprises receiving a portion of the interventional instrument into the central lumen, moving the interventional instrument in a first direction along the longitudinal axis, unlocking a linkage from an adjacent linkage, and directing the unlocked linkage in a second direction opposite the first direction into a return assembly.

In one aspect, unlocking a linkage from an adjacent linkage comprises applying force to the linkage to displace a projection of the linkage from a recess of the adjacent linkage.

In one aspect, unlocking a linkage from an adjacent linkage comprises applying force to the linkage to pivot the linkage at a hinge mechanism coupling the linkage to an adjacent linkage.

In one aspect, directing the unlocked linkage in a second direction opposite the first direction into a return assembly comprises rotating the unlocked linkage away from the central lumen.

In one aspect, directing the unlocked linkage in a second direction opposite the first direction into a return assembly comprises sliding the unlocked linkage in the first direction toward an adjacent linkage.

In one aspect, directing the unlocked linkage in a second direction opposite the first direction into a return assembly comprises shortening the first length of the variable-length support assembly to a second length of the variable-length support assembly.

In another embodiment, the present disclosure is directed to an apparatus for guiding an elongated flexible instrument, the apparatus comprising a first plurality of linkages forming a first side of a channel of a support assembly, a second plurality of linkages forming a second side of the channel, opposite the first side, a third plurality of linkages interlocked between the first and second plurality of linkages and forming a third side of the channel, and a fourth plurality of linkages interlocked between the first and second plurality of linkages and forming a fourth side of the channel, opposite the third side. Advancement of the support assembly along a longitudinal axis defined through the channel causes an asynchronous unlocking of the first, second, third, and fourth plurality of linkages from each other.

In another embodiment, the present disclosure is directed to an apparatus for guiding an elongated flexible instrument, the apparatus comprising a plurality of linkages, each coupled by a hinge to an adjacent linkage of the plurality of linkages. The plurality of linkages have an elongated configuration in which the plurality of linkages are helically wound with each linkage of the plurality of linkages interlocked with a non-adjacent linkage to form a channel of a variable-length support assembly. In one aspect, the plurality of linkages have a splayed configuration in which each linkage of the plurality of linkages is unlocked from the non-adjacent linkage and is rotated about and translated along an axis of the hinge relative to the adjacent linkage of the plurality of linkages.

In another embodiment, the present disclosure is directed to an apparatus for guiding an elongated flexible instrument, the apparatus comprising a first plurality of linkages forming a first side of a channel of a support assembly and a second plurality of linkages forming a second side of the channel, opposite the first side. In one aspect, in an elongated configuration of the support assembly, each linkage of the first plurality of linkages is interlocked between two linkages of the second plurality of linkages, and each linkage of the first plurality of linkages is hingedly coupled to an adjacent linkage of the first plurality of linkages by a bridging element that maintains a spacing between the linkage and the adjacent linkage. The support assembly transitions from the elongated configuration to a separated configuration as the support assembly is advanced along a longitudinal axis defined by the channel, and, in the separated configuration, each linkage of the plurality of linkages is unlocked from between the two linkages of the second plurality of linkages.

Additional aspects, features, and advantages of the present disclosure will become apparent from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 2A is a simplified diagram of a medical instrument system according to some embodiments of the present disclosure.

FIG. 2B is a simplified diagram of a medical instrument with an extended medical tool according to some embodiments of the present disclosure.

FIG. 3 is a simplified diagram of a side view of a teleoperational manipulator assembly, an elongate instrument, and an instrument guiding apparatus according to some embodiments of the present invention.

FIG. 4 illustrates a schematic side view of the distal end of the instrument guiding apparatus of FIG. 3 in an initial configuration.

FIGS. 5A and 5B illustrate perspective views of an exemplary linkage subset according to one embodiment of the present disclosure. FIG. 5A illustrates a perspective view of the linkage subset in a partially "unzipped" or inactive configuration. FIG. 5B illustrates a more detailed perspective view of particular linkages of the exemplary linkage subset shown in FIG. 5A.

Figure 6C:
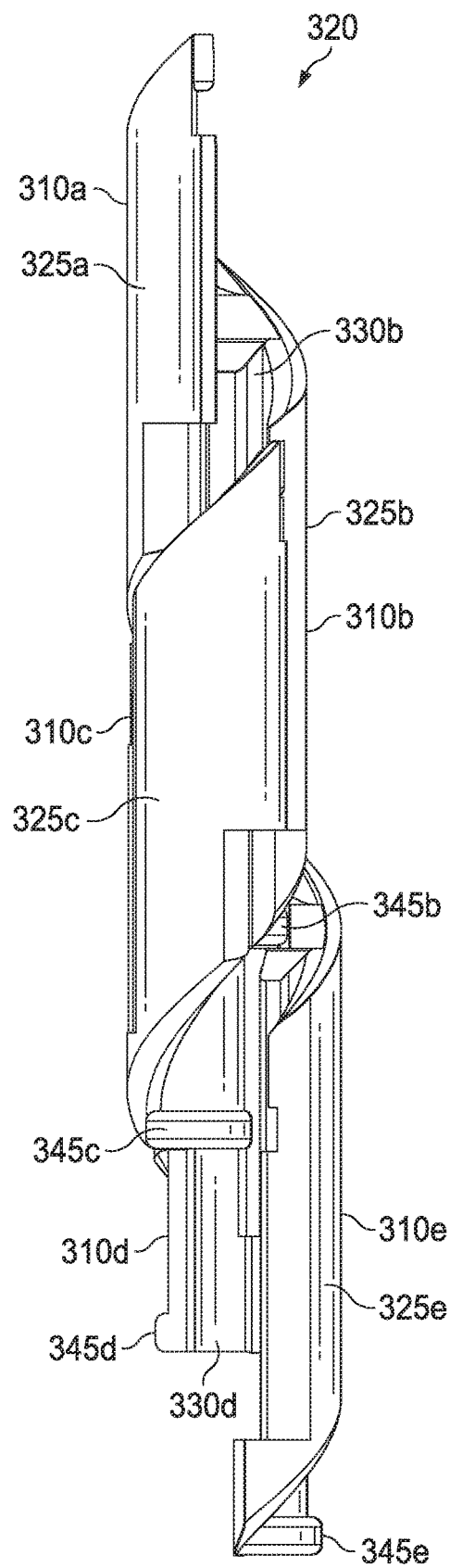
Figure 6D:
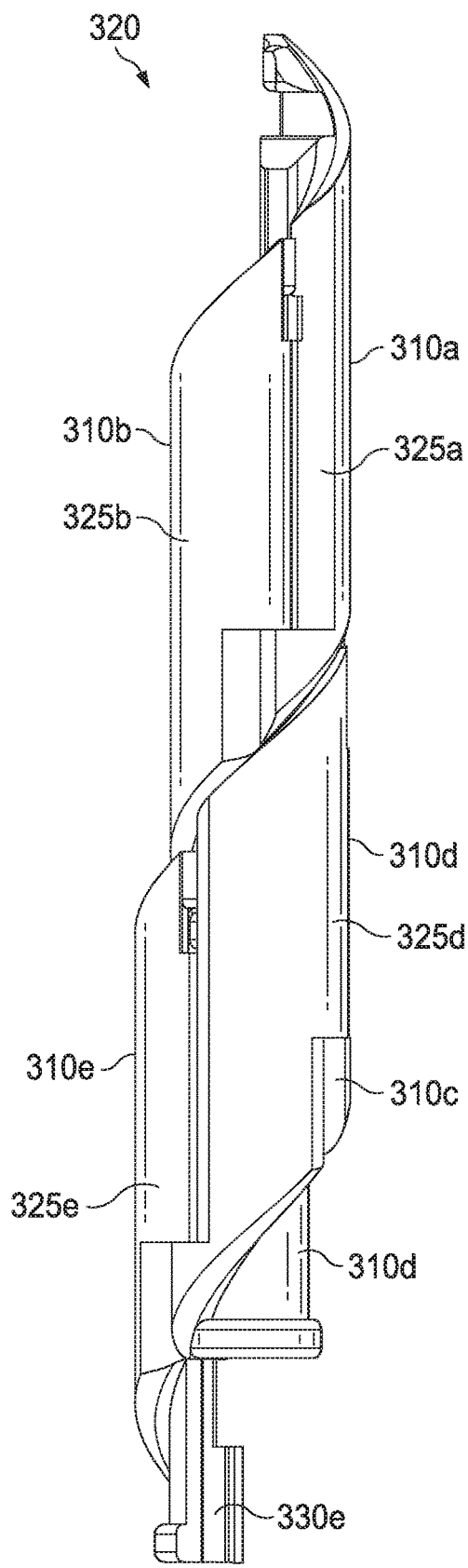
Figure 6E:
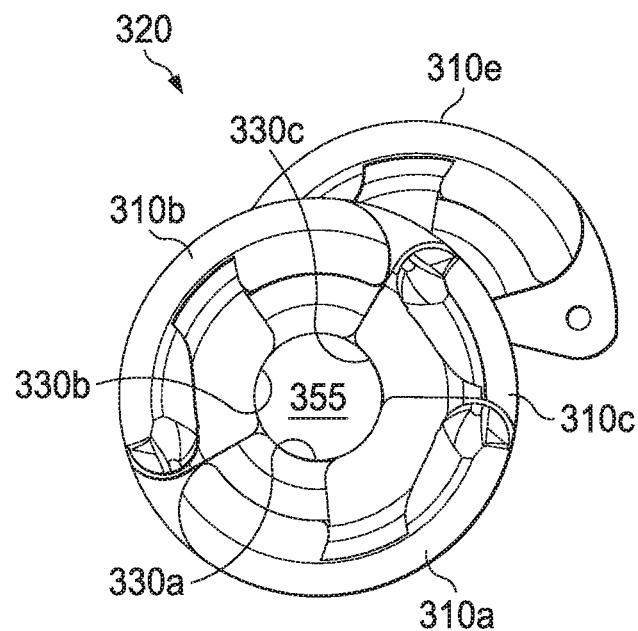
Figure 6F:
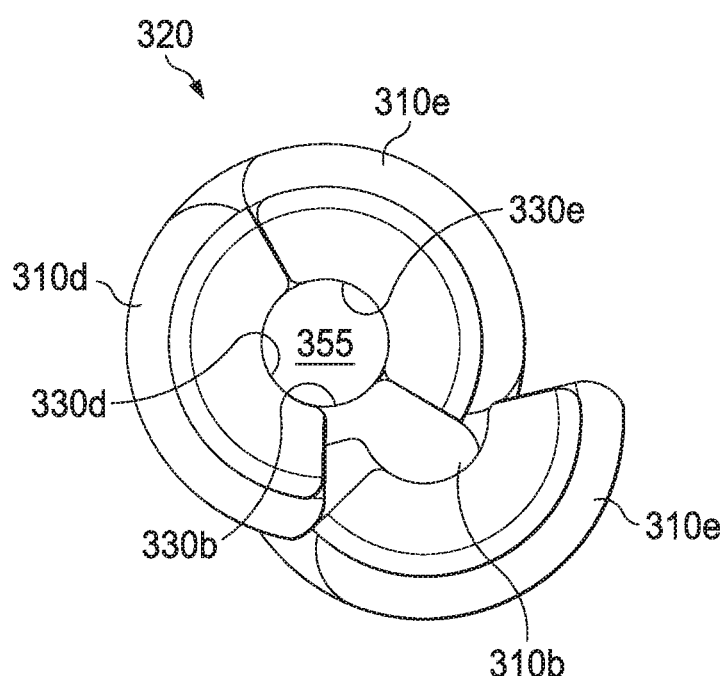
Figure 6G:
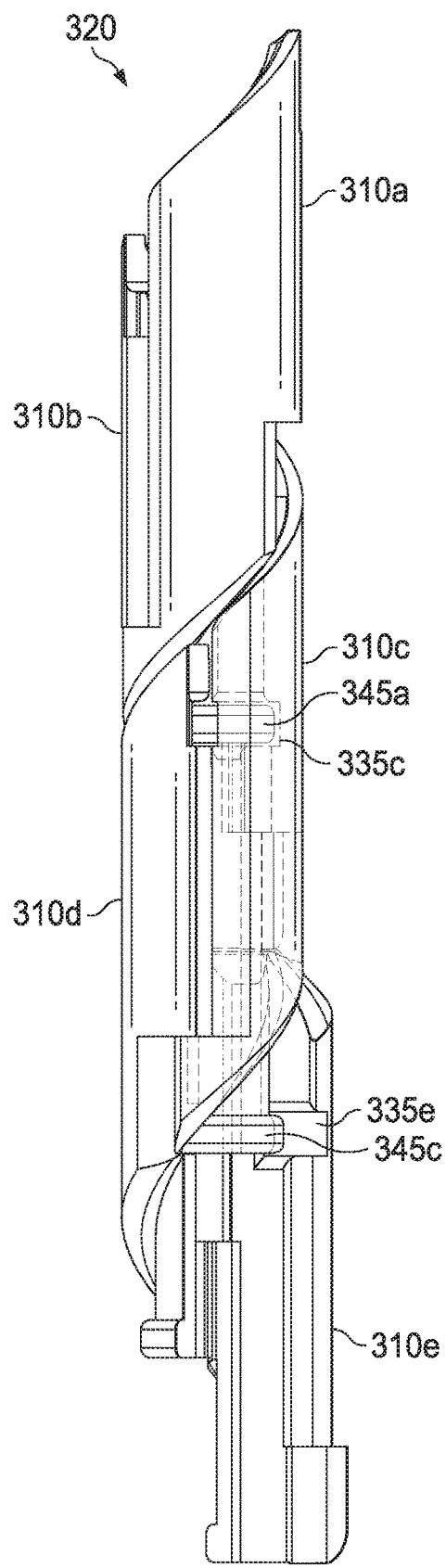
Figure 6H:
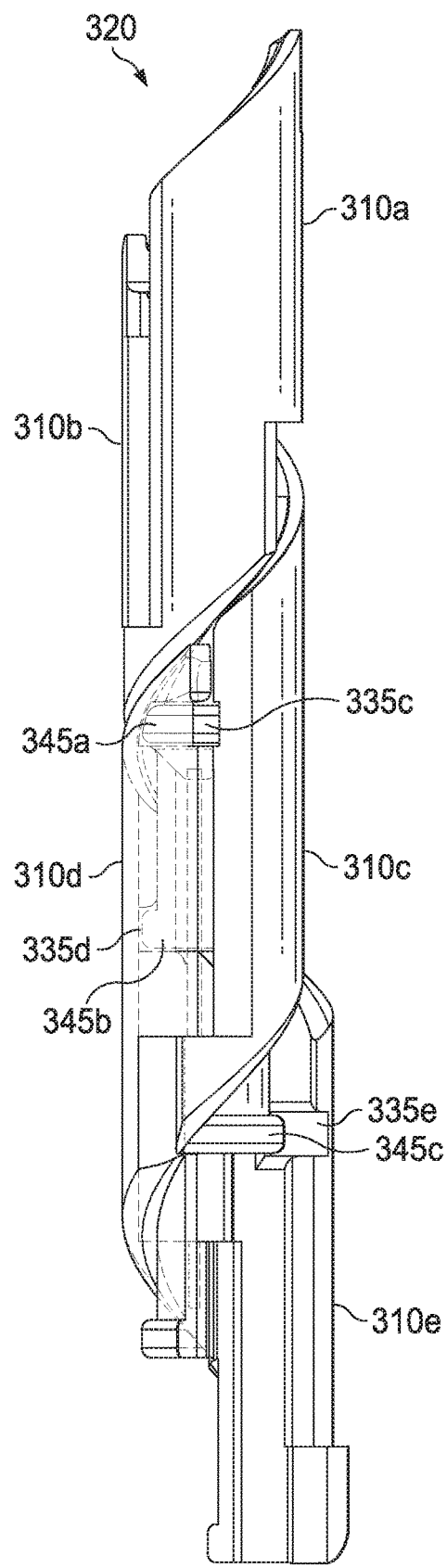

FIGS. 6A-6H illustrate various views of the linkage subset illustrated in FIG. 5A. In particular. FIG. 6A illustrates a front view of the linkage subset illustrated in FIG. 5A. FIG. 6B illustrates a back view of the linkage subset illustrated in FIG. 5A. FIG. 6C illustrates a right side view of the linkage subset illustrated in FIG. 5A. FIG. 6D illustrates a left side view of the linkage subset illustrated in FIG. 5A. FIG. 6E illustrates a top view of the linkage subset illustrated in FIG. 5A. FIG. 6F illustrates a bottom view of the linkage subset illustrated in FIG. 5A. FIGS. 6G and 6H illustrate front, partially transparent views of the linkage subset 320.

Figure 7A:
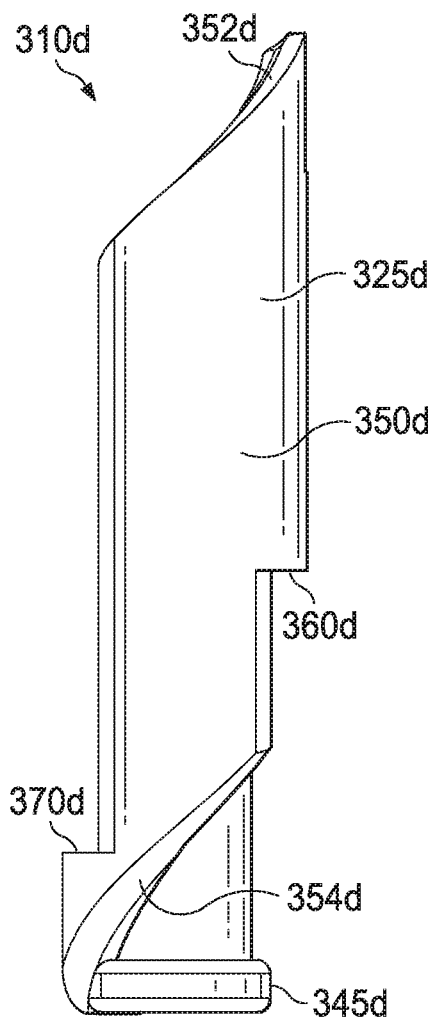
Figure 7B:
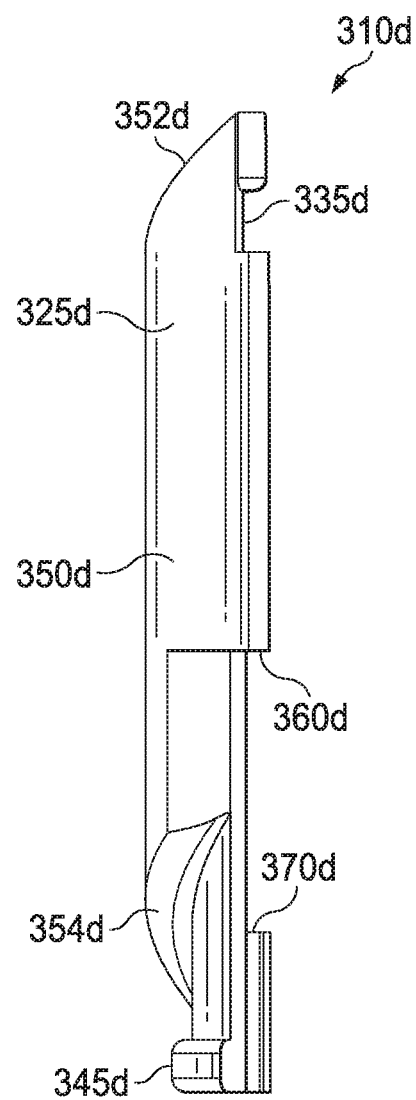
Figure 7C:
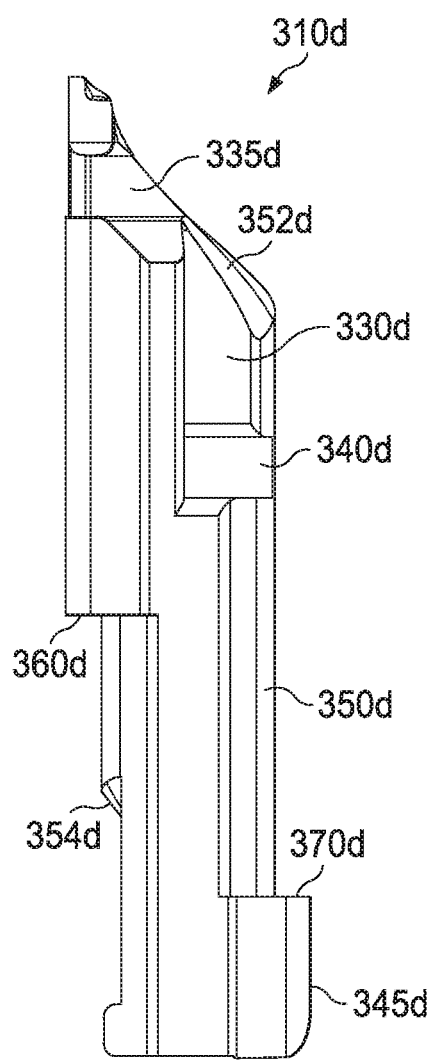
Figure 7D:
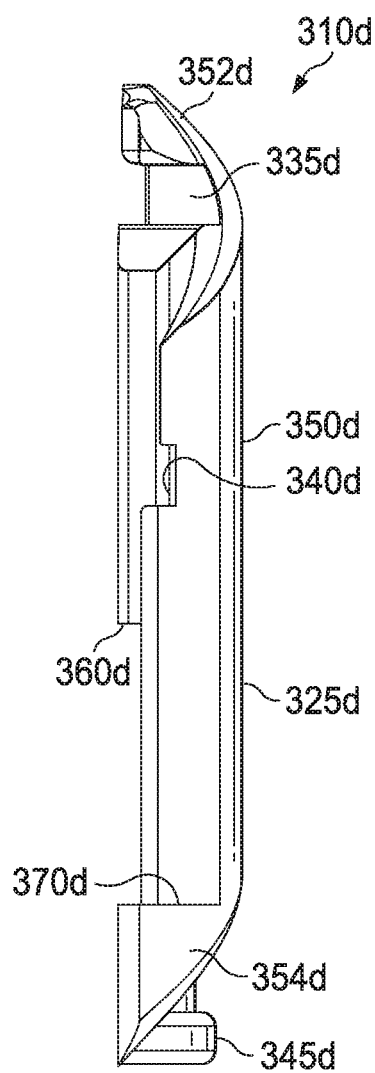
Figure 7E:
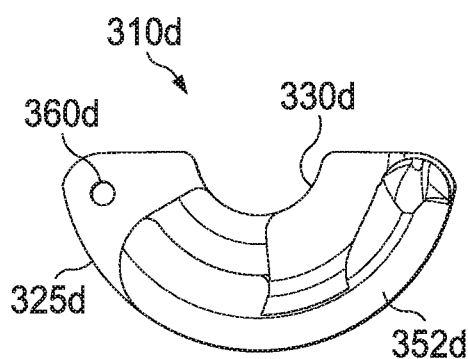
Figure 7F:
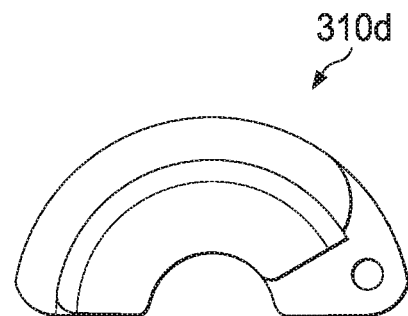

FIGS. 7A-7F illustrate various views of an exemplary linkage of the linkage subset illustrated in FIG. 5A. FIG. 7A illustrates a front view of the linkage. FIG. 7B illustrates a back view of the linkage. FIG. 7C illustrates a right side view of the linkage. FIG. 7D illustrates a left side view of the linkage. FIG. 7E illustrates a top view of the linkage. FIG. 7F illustrates a bottom view of the linkage.

Figure 8A:
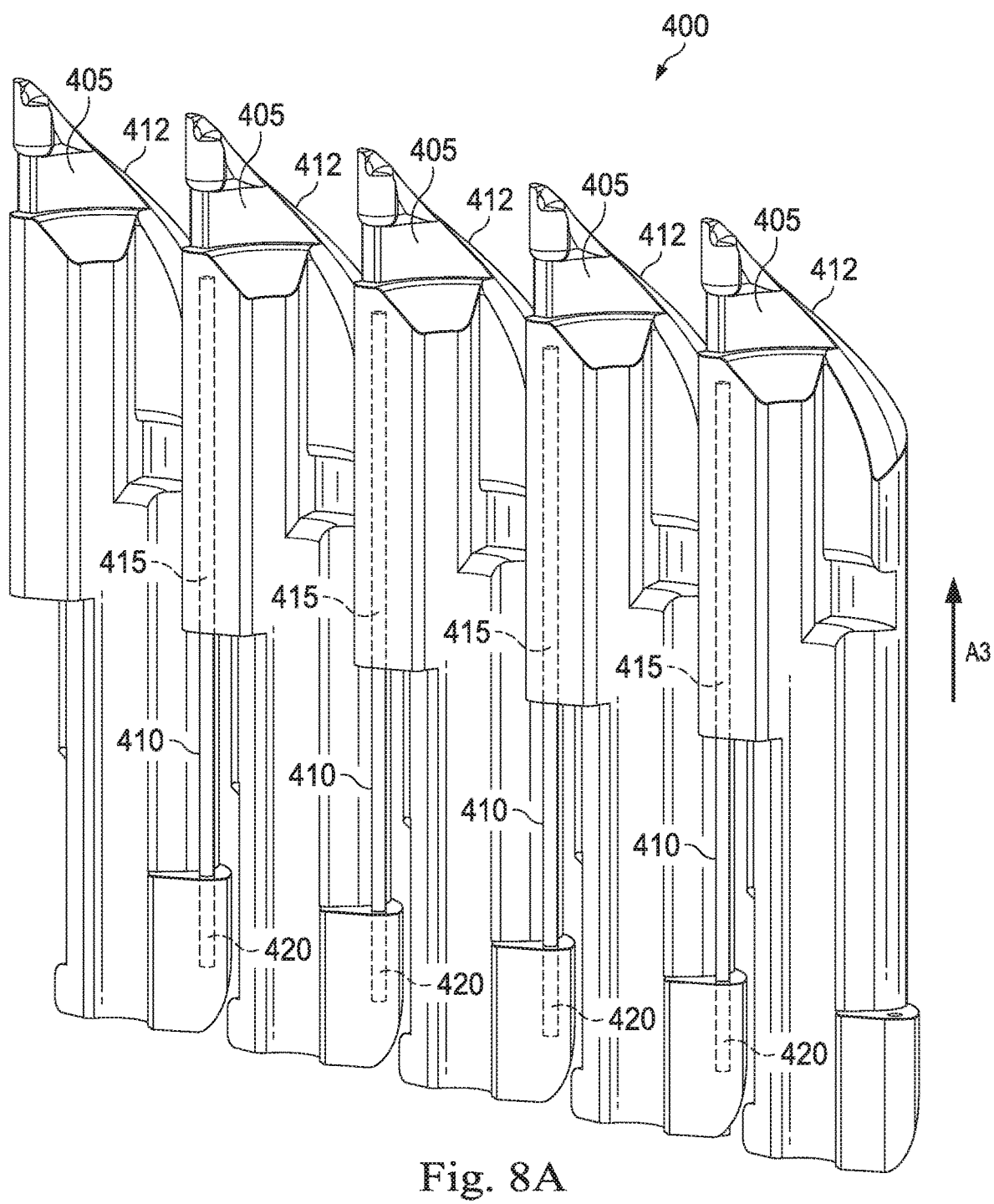
Figure 8B:
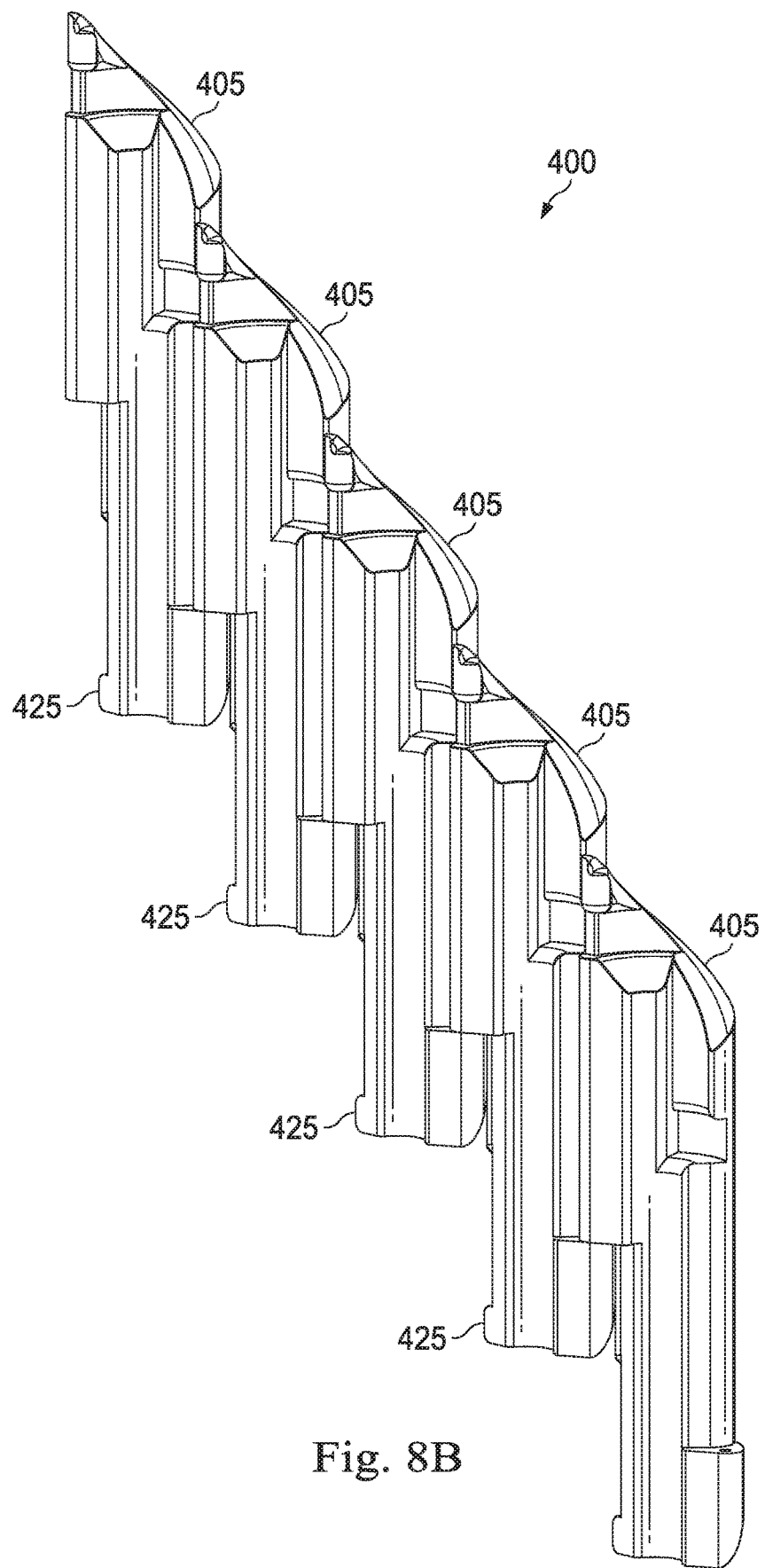

FIGS. 8A and 8B illustrate an exemplary linkage subset of an instrument guiding apparatus according to an embodiment of the present disclosure. FIG. 8A illustrates the exemplary linkage subset in a compact configuration. FIG. 8B illustrates the exemplary linkage subset in an expanded configuration.

Figure 9A:
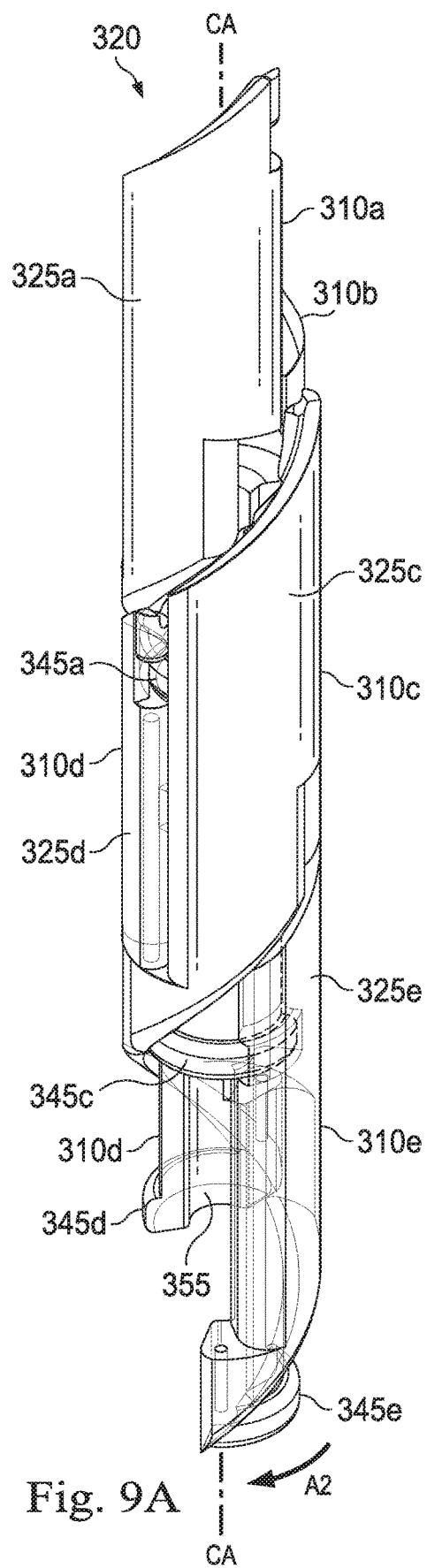
Figure 9B:
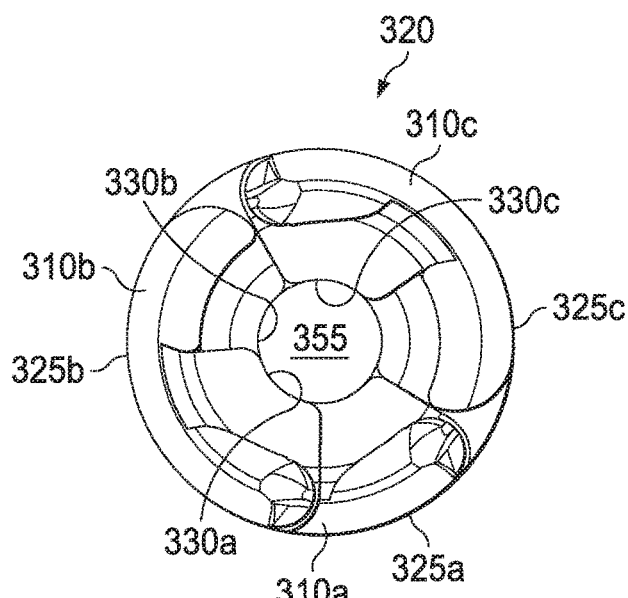

FIGS. 9A and 9B illustrate the linkage subset shown in FIG. 5A in a "zipped" or active configuration. FIG. 9A illustrates a partially transparent perspective view of the linkage subset, and FIG. 9B illustrates a top view of the linkage subset.

Figure 10:
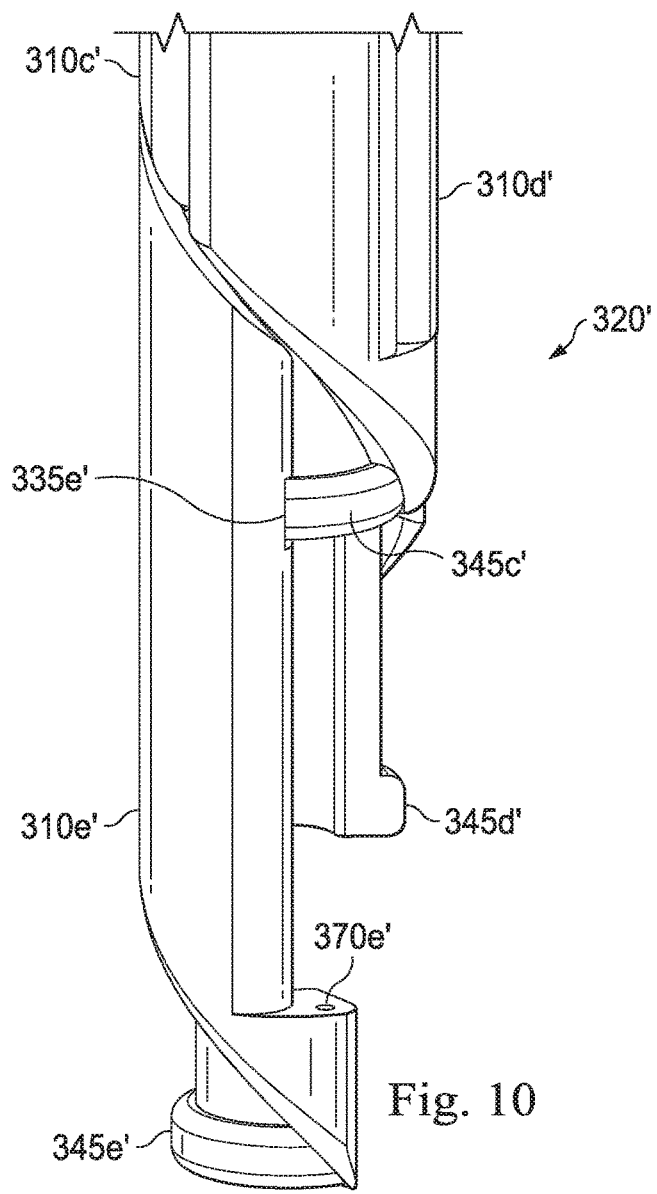

FIG. 10 illustrates a perspective view of an exemplary linkage subset of an instrument guiding apparatus according to an embodiment of the present disclosure.

Figure 11:
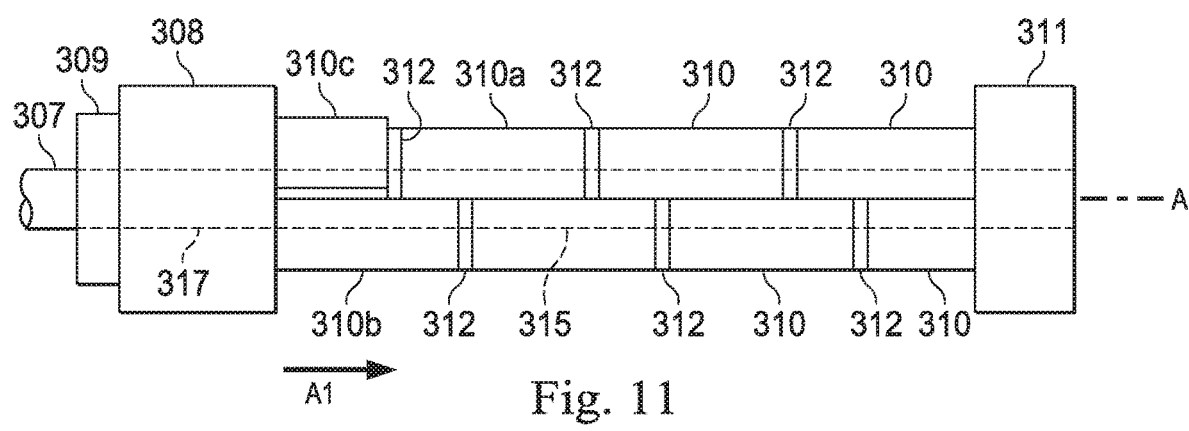

FIG. 11 illustrates a schematic side view of the distal end of the instrument guiding apparatus of FIG. 4 in a partially "unzipped" or inactive configuration according to an embodiment of the present invention.

FIG. 12 illustrates the interventional instrument and instrument guiding apparatus of FIGS. 3 and 4 coupled to a teleoperational manipulator assembly in a patient environment according to an embodiment of the present invention.

Figure 13C:
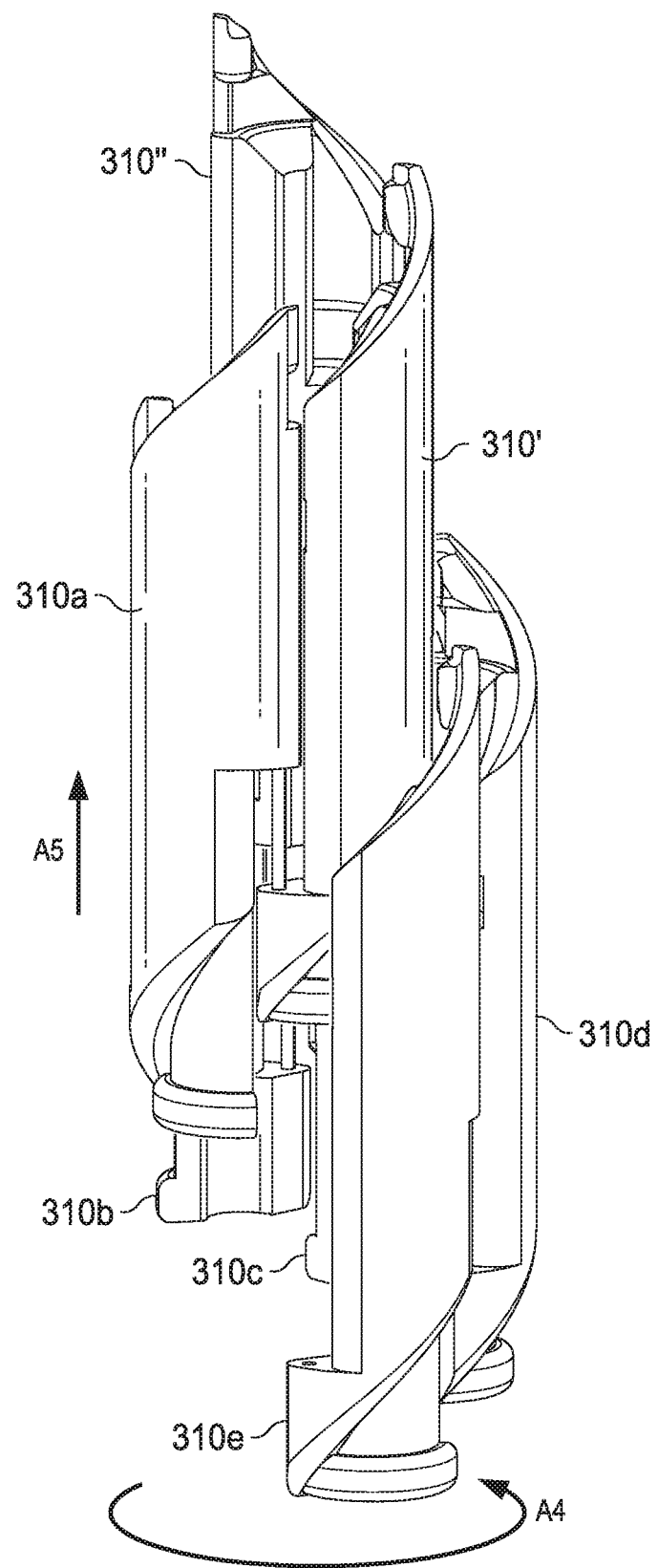

FIGS. 13A-13C illustrate side views of an exemplary instrument guiding apparatus including the linkage subset shown in FIG. 5A according to one embodiment of the present disclosure.

Figure 14:
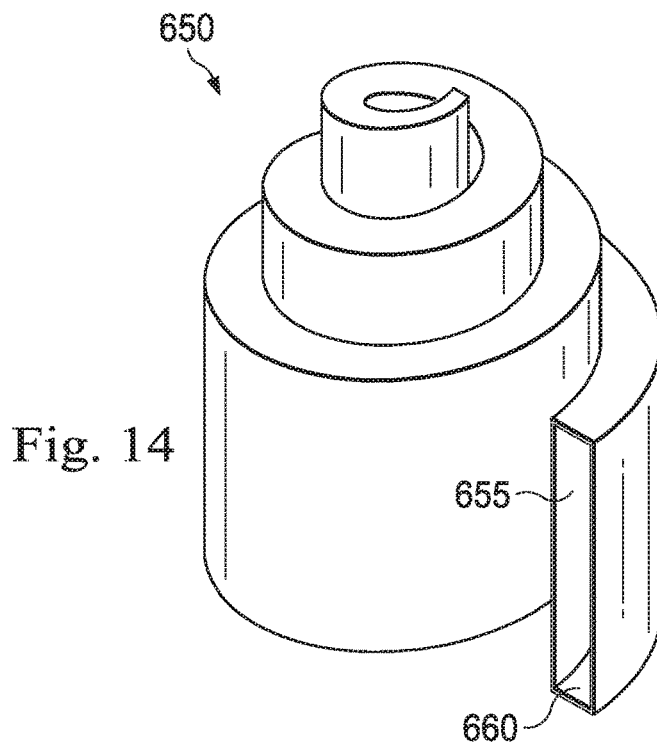

FIG. 14 illustrates an exemplary return assembly according to one embodiment of the present disclosure.

Figure 15:
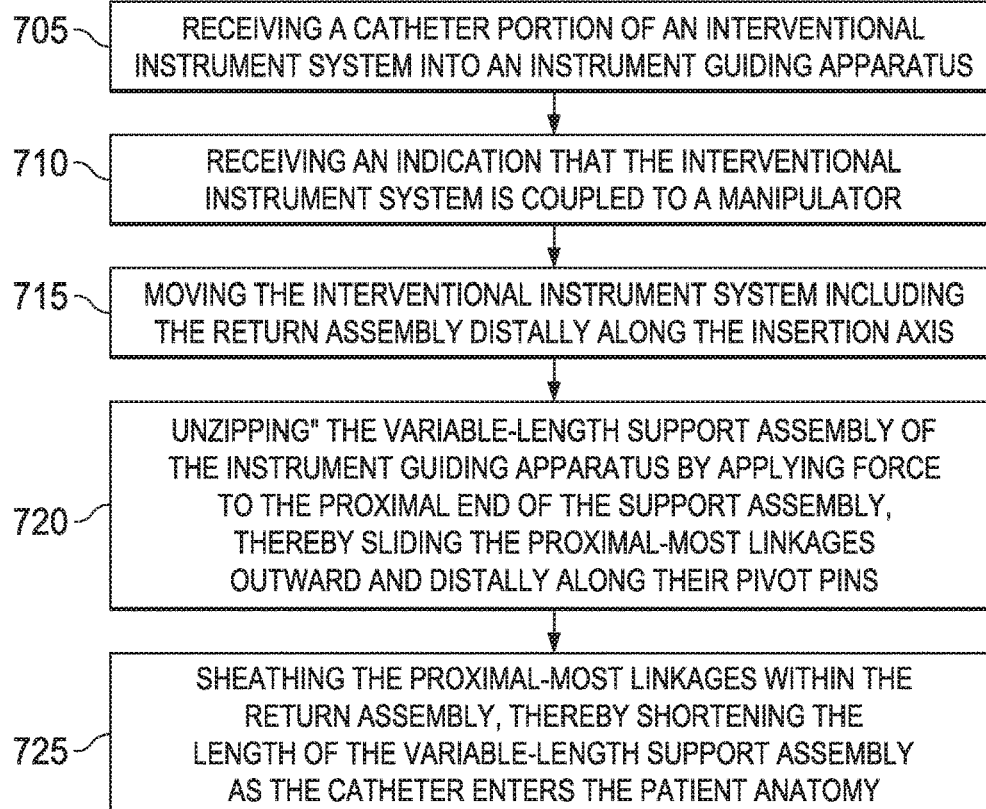

FIG. 15 is a flowchart describing a method of guiding an interventional instrument according to an embodiment of the present disclosure.

Figure 16A:
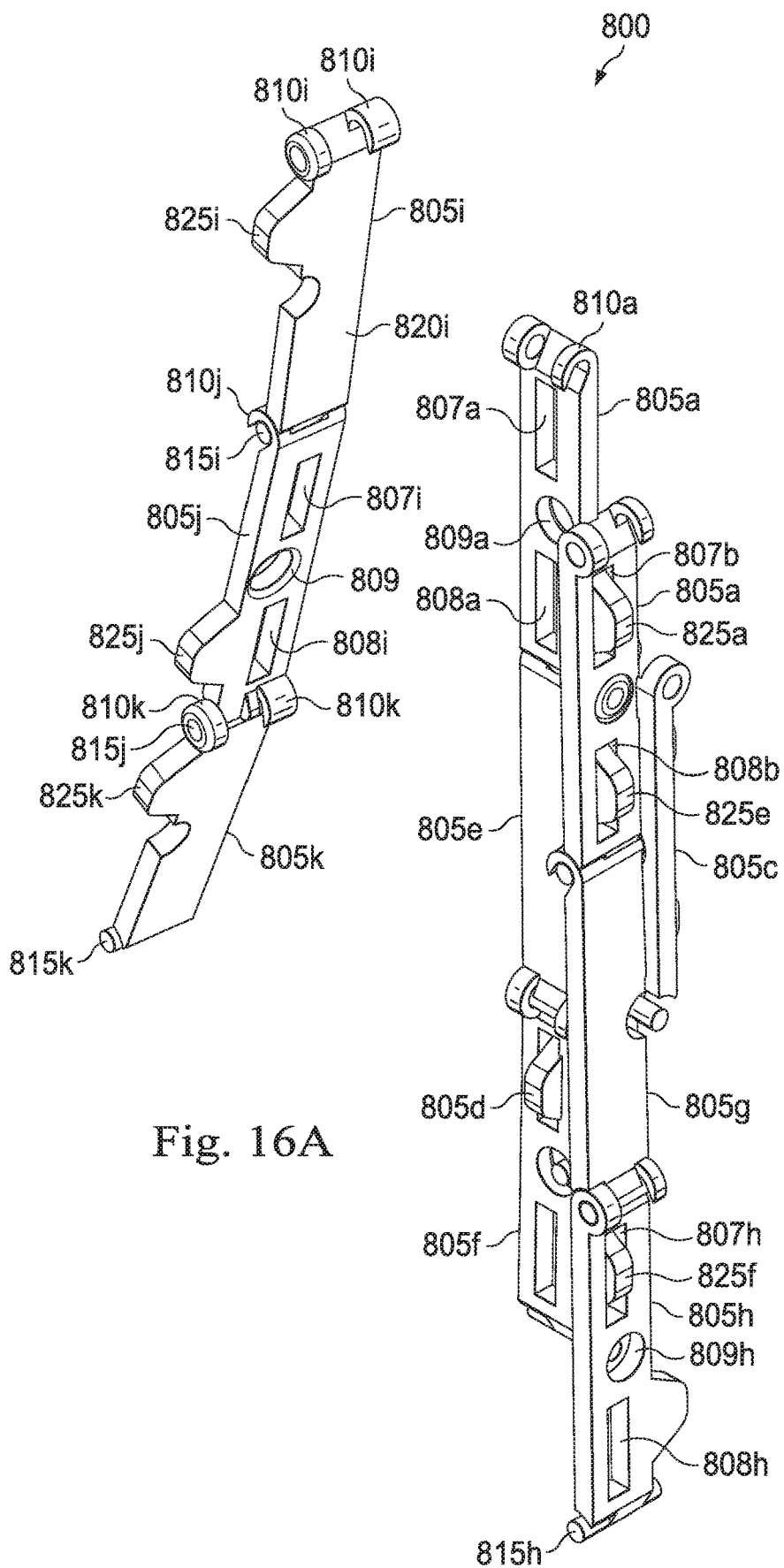
Figure 16B:
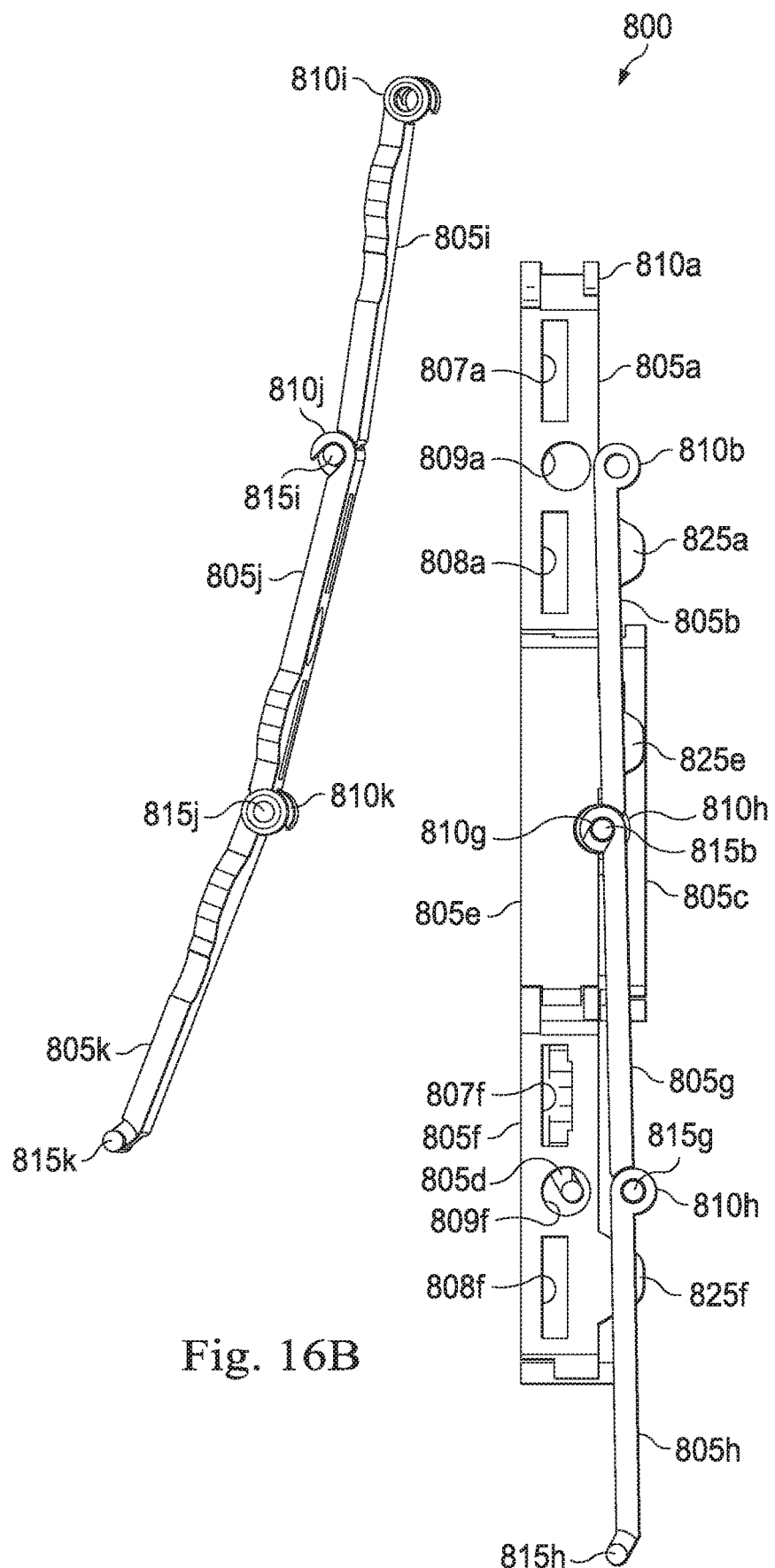
Figure 16C:
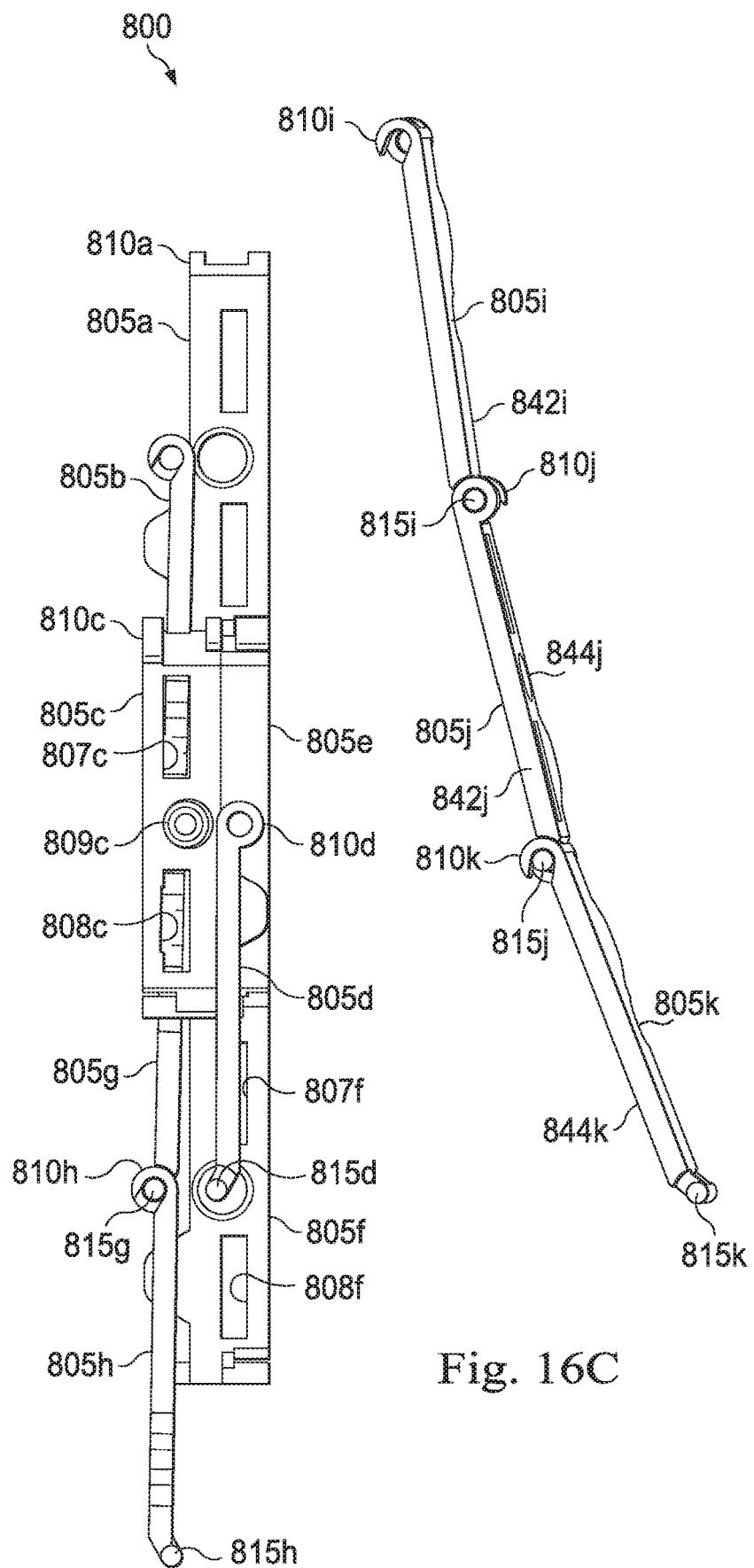
Figure 16D:
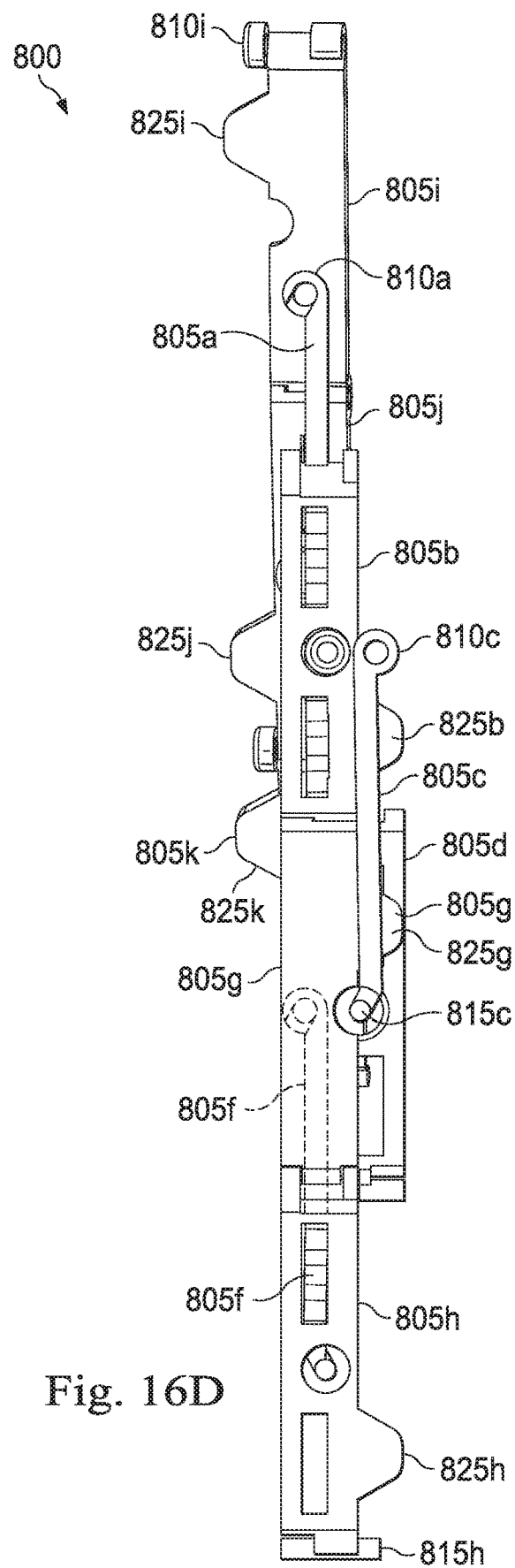
Figure 16E:
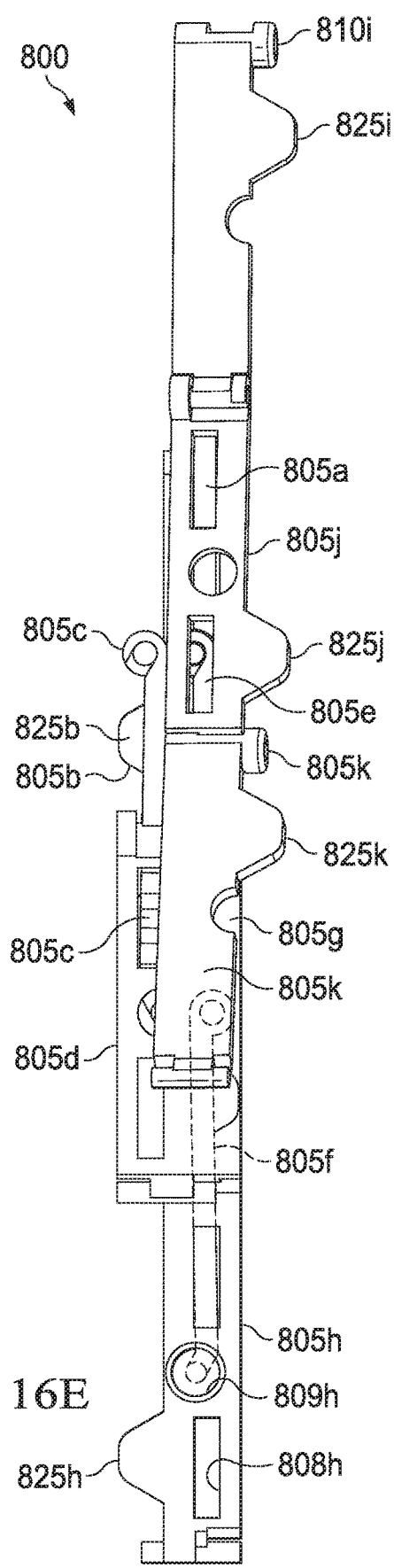
Figure 16F:
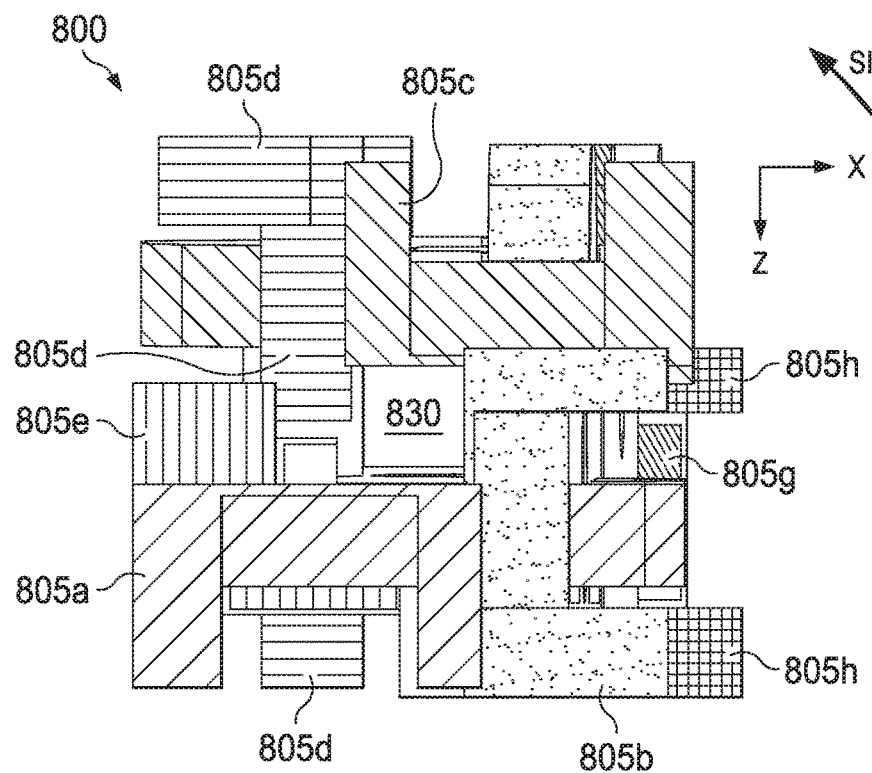

FIGS. 16A-16G illustrate various views of an exemplary linkage subset. In particular, FIG. 16A illustrates a front view of the linkage subset. FIG. 6B illustrates a back view of the linkage subset. FIG. 16C illustrates a right side view of the linkage subset. FIG. 16D illustrates a left side view of the linkage subset. FIG. 16E illustrates a top view of the linkage subset. FIG. 16F illustrates a bottom view of the linkage subset.

Figure 16G:
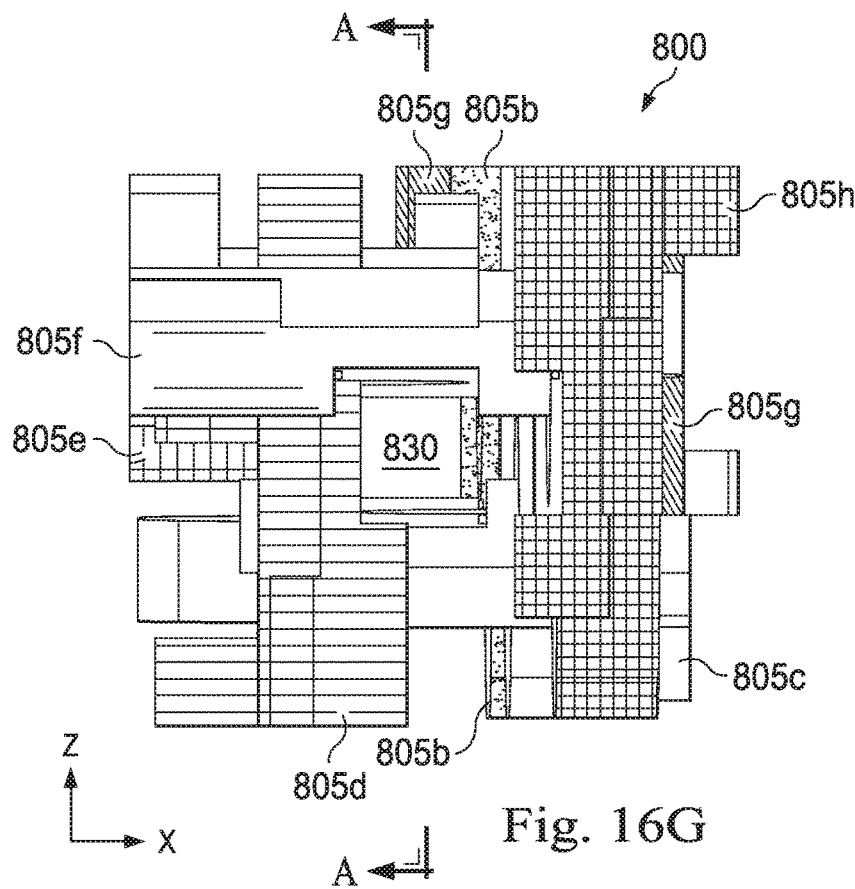
Figure 17:
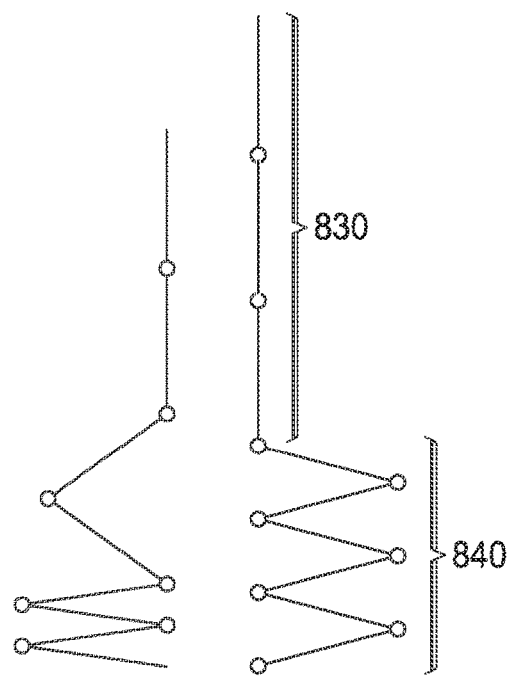

FIG. 17 illustrates a schematic diagram of the unfolding and folding mechanism of the linkage subset illustrated in FIGS. 16A-16G as it transitions from an active to an inactive configuration.

Figure 18:
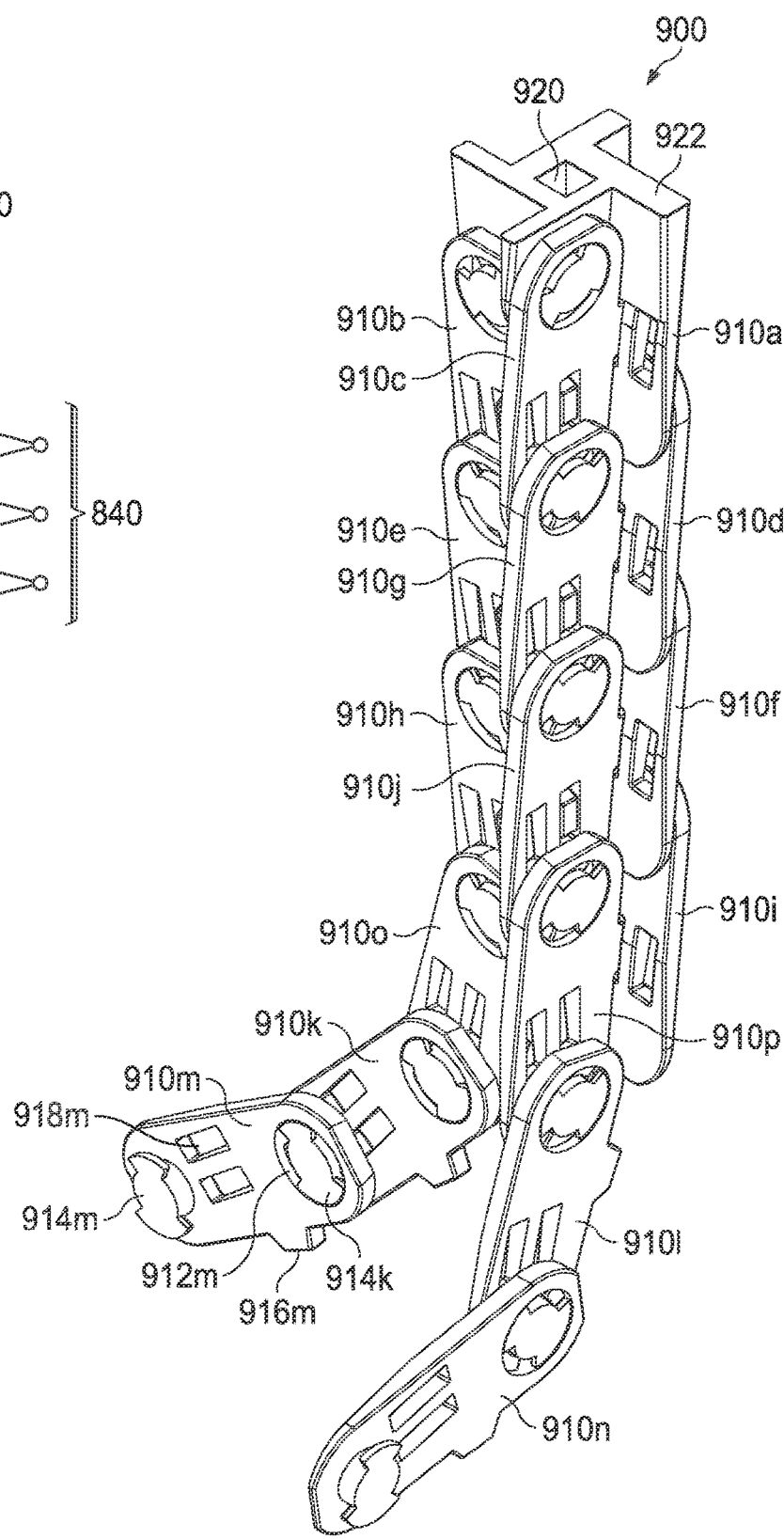

FIG. 18 illustrates a perspective view of an exemplary linkage subset according to another embodiment of the present disclosure.

Figure 19A:
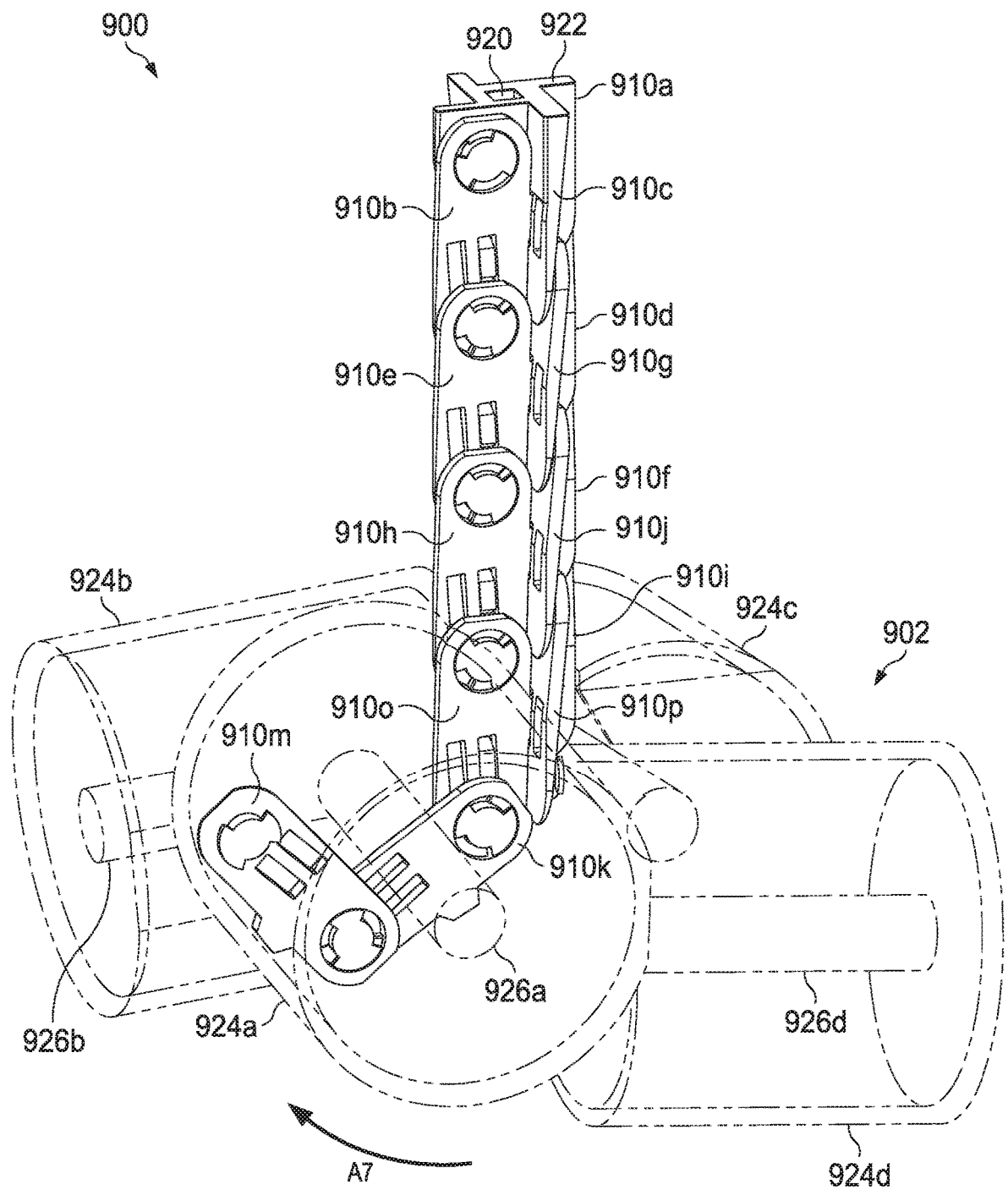
Figure 19B:
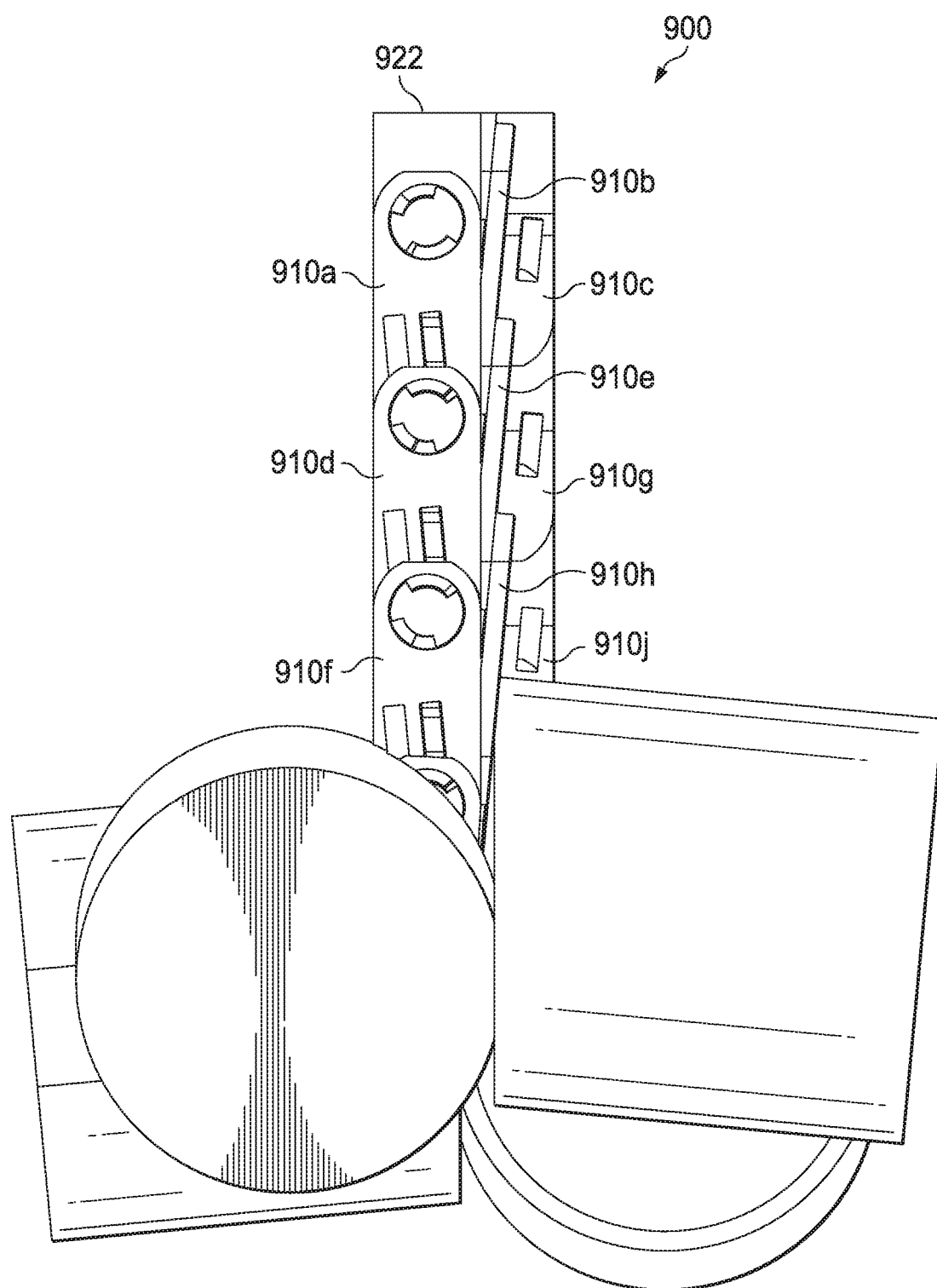
Figure 19C:
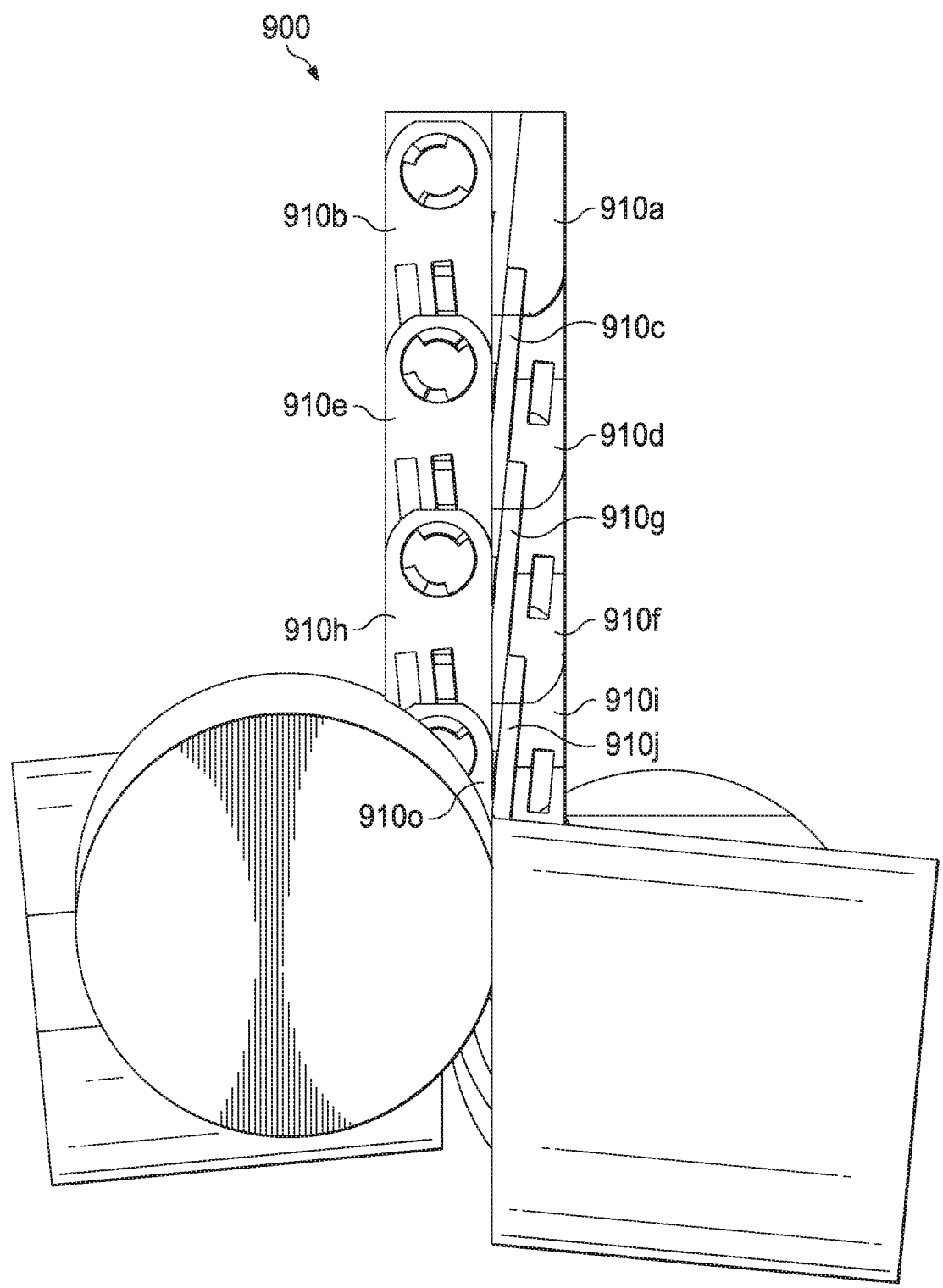
Figure 19D:
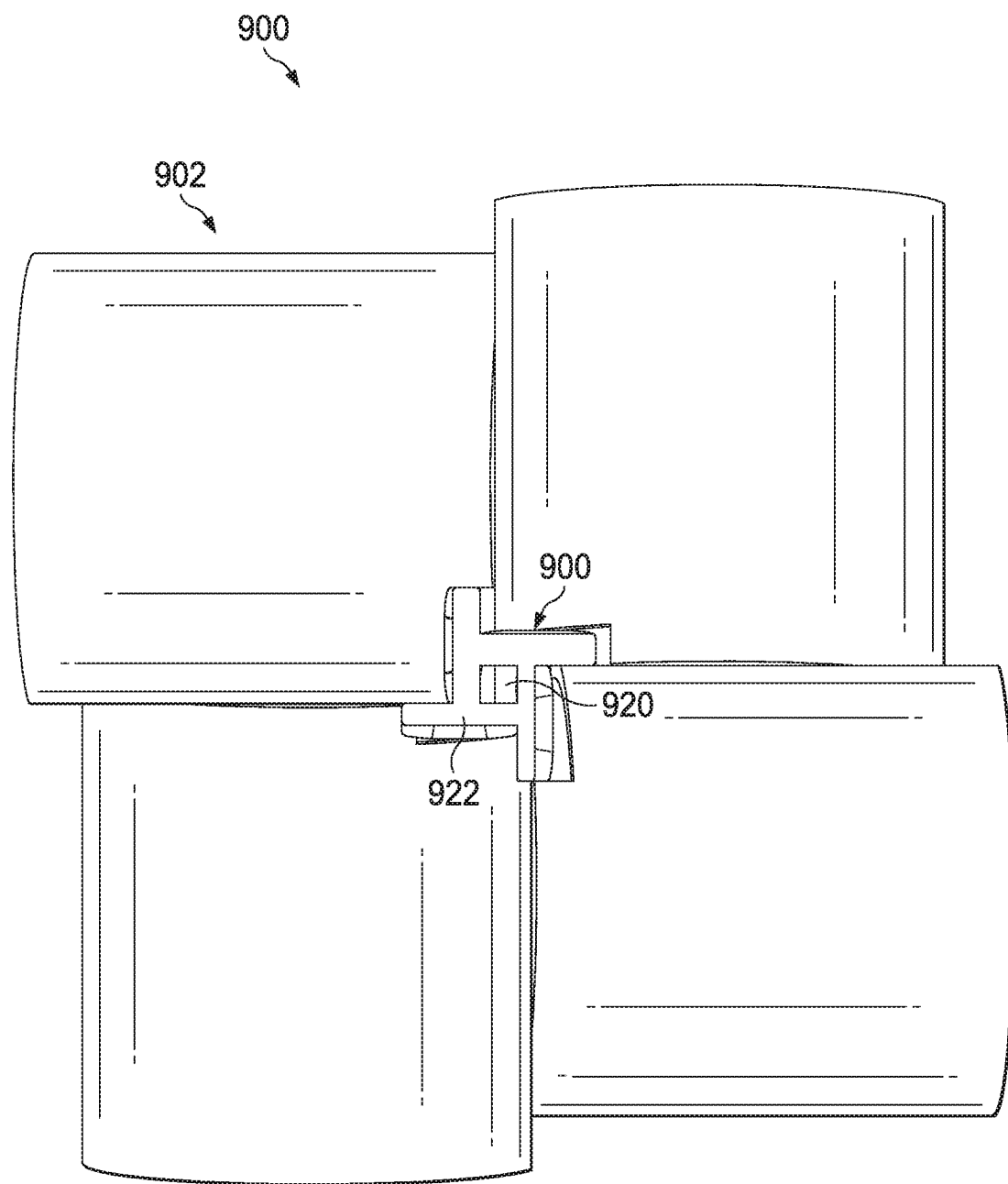
Figure 19E:
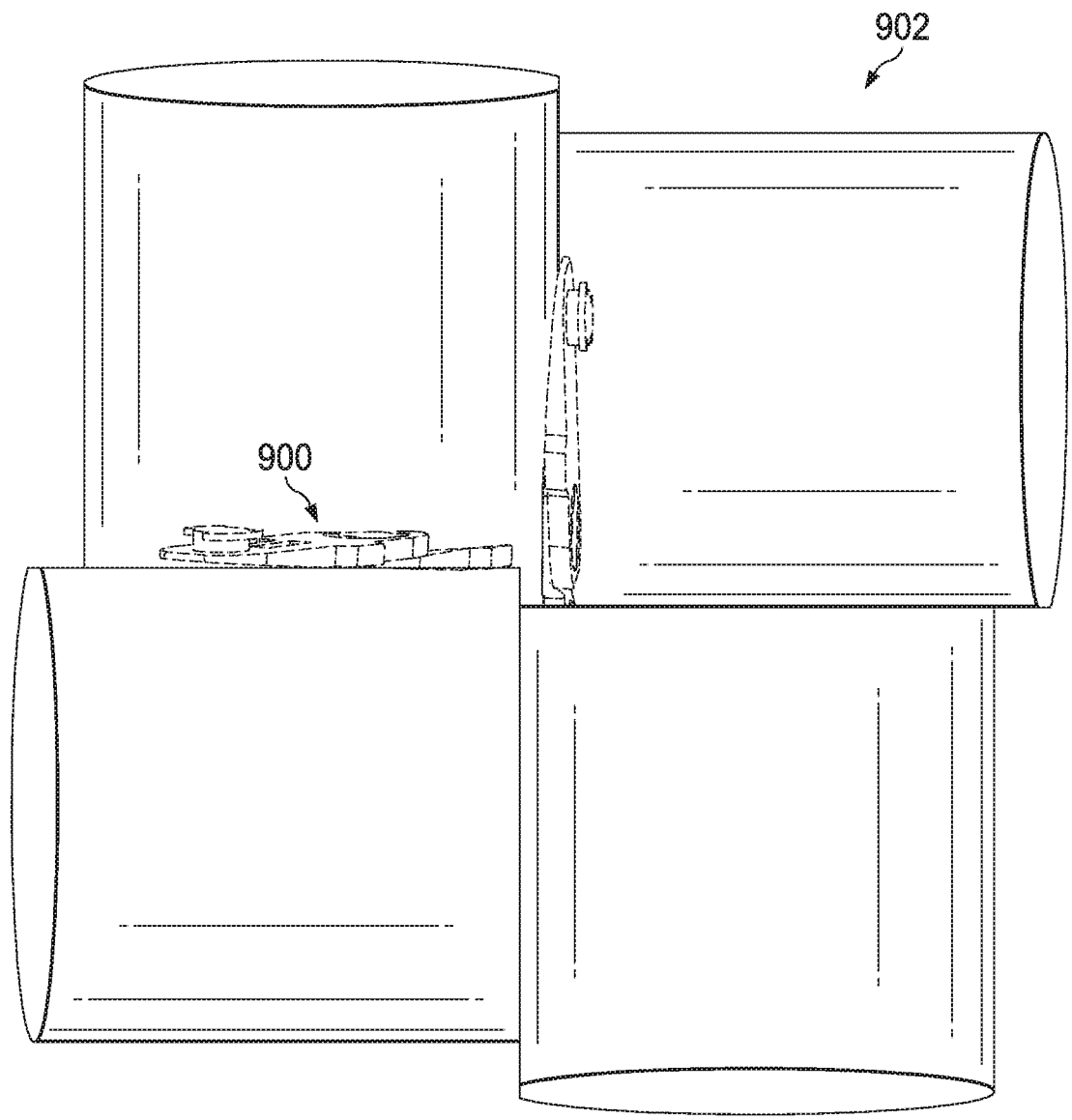

FIGS. 19A-19E illustrate various views of the exemplary linkage subset shown in FIG. 18 coupled to an exemplary return assembly. In particular. FIG. 19A illustrates a front view of the linkage subset and return assembly. FIG. 19B illustrates a back view of the linkage subset and return assembly. FIG. 19C illustrates a right side view of the linkage subset and return assembly. FIG. 19D illustrates a top view of the linkage subset and return assembly. FIG. 19E illustrates a bottom view of the linkage subset and return assembly.

Figure 20:
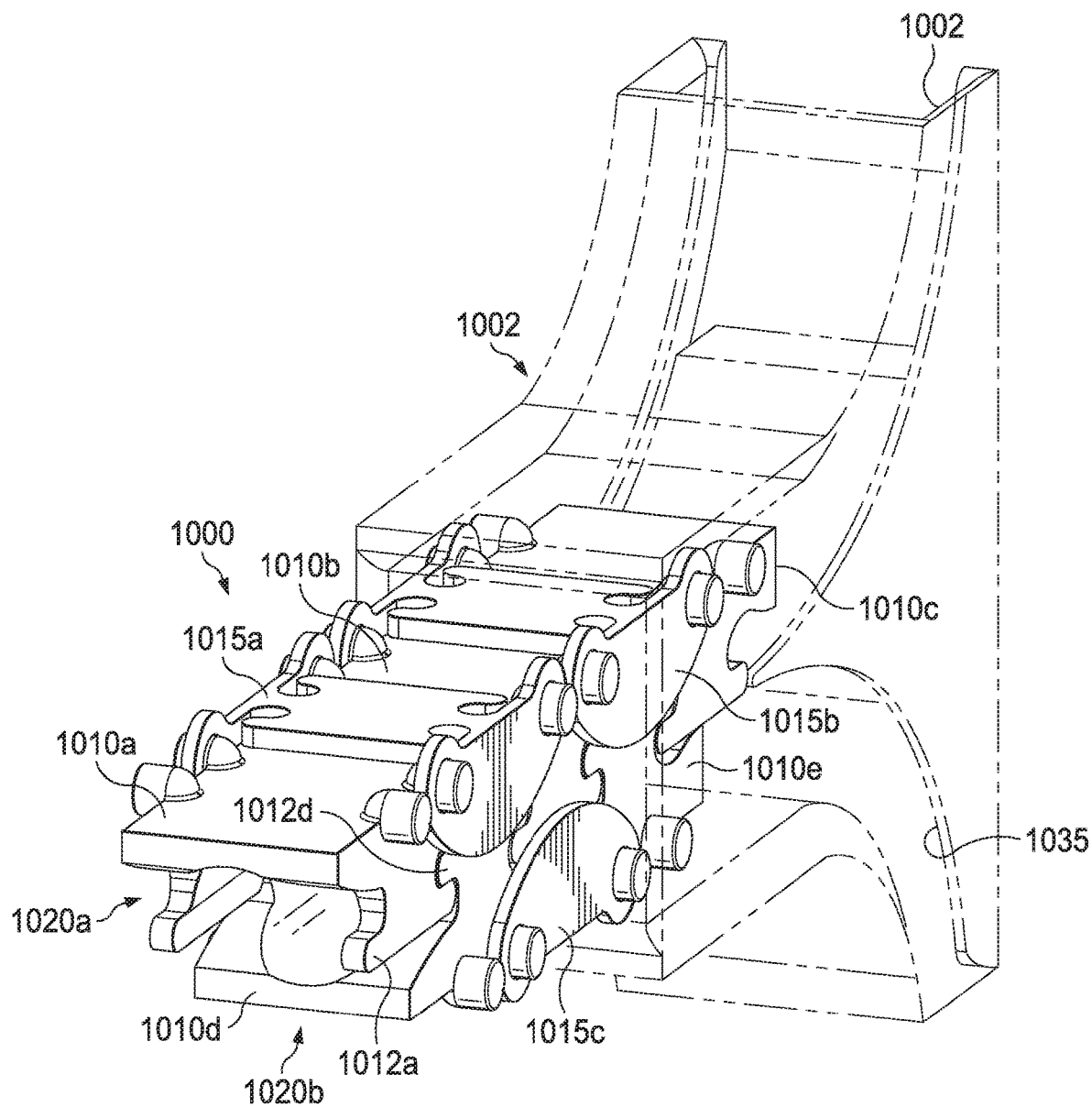

FIG. 20 illustrates a perspective view of an exemplary linkage subset coupled to an exemplary return assembly.

Figure 21A:
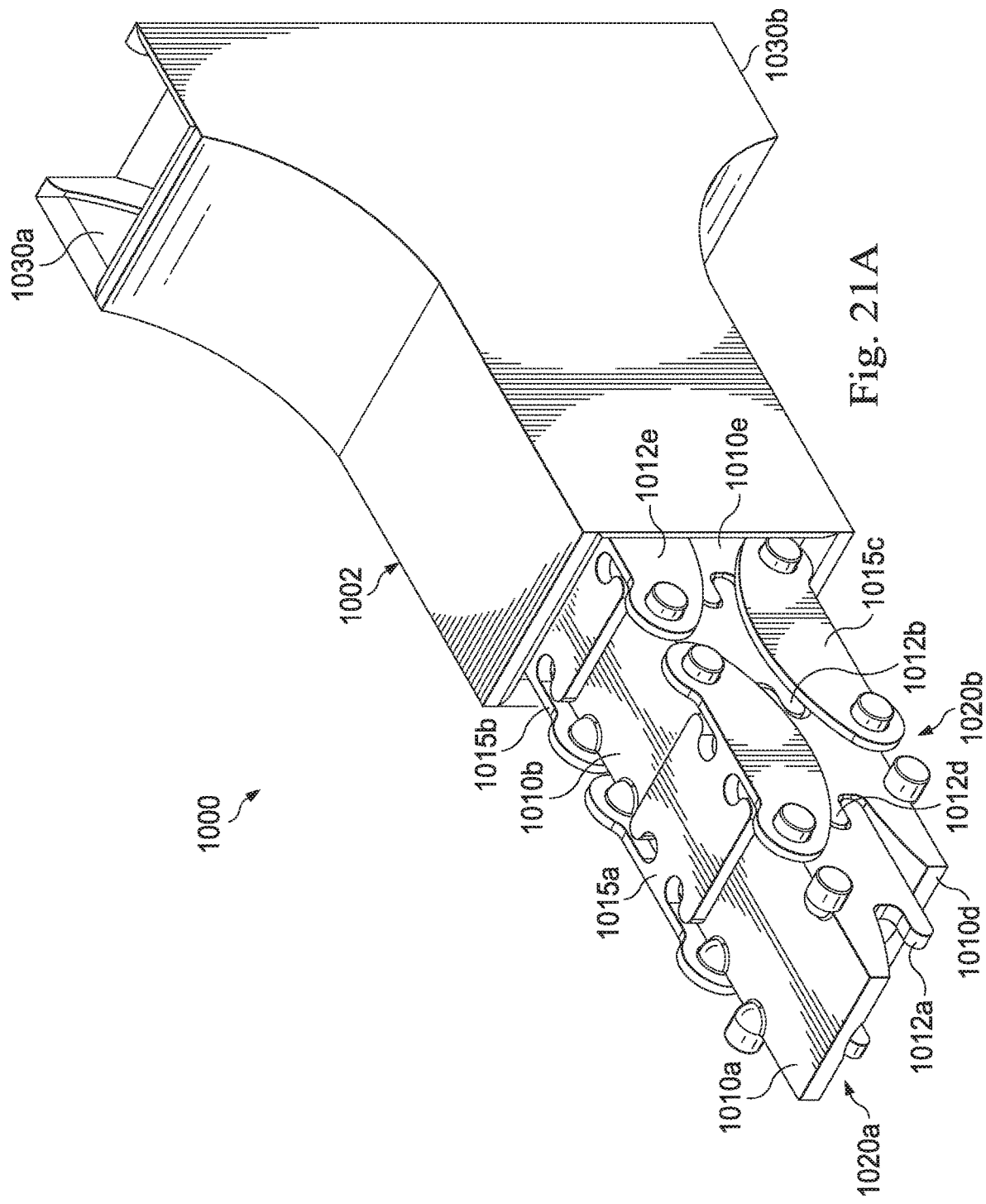
Figure 21B:
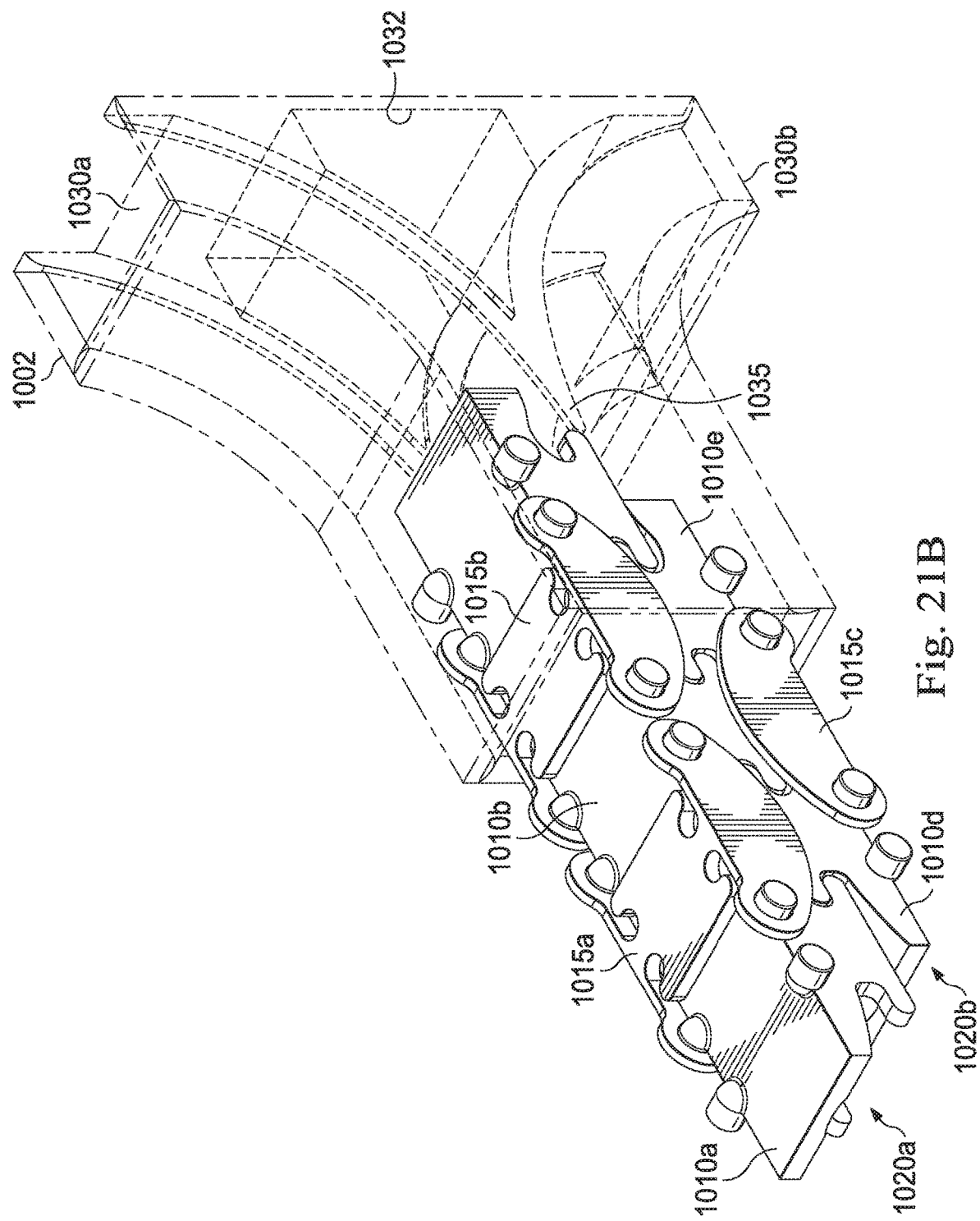
Figure 21C:
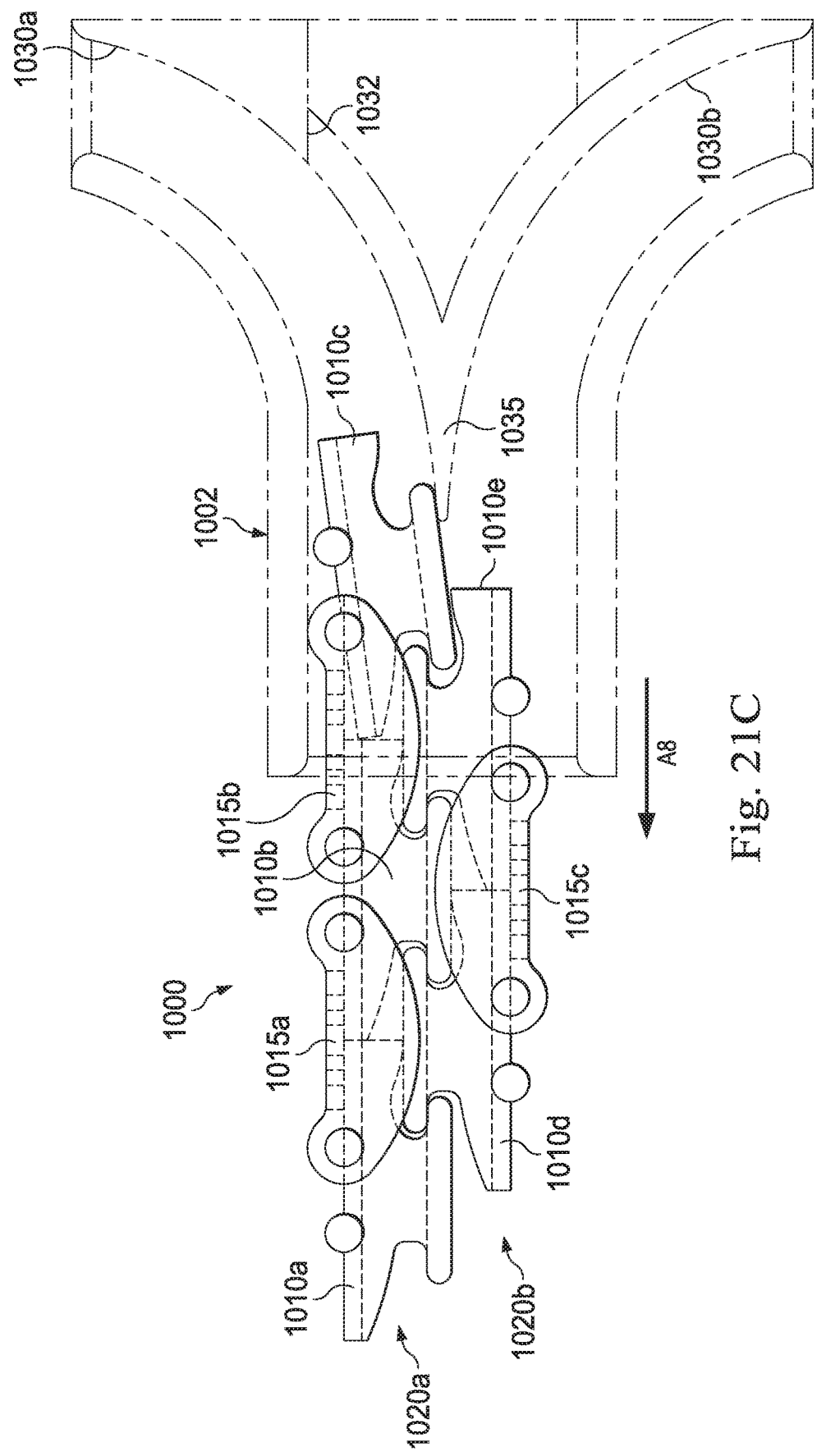
Figure 21D:
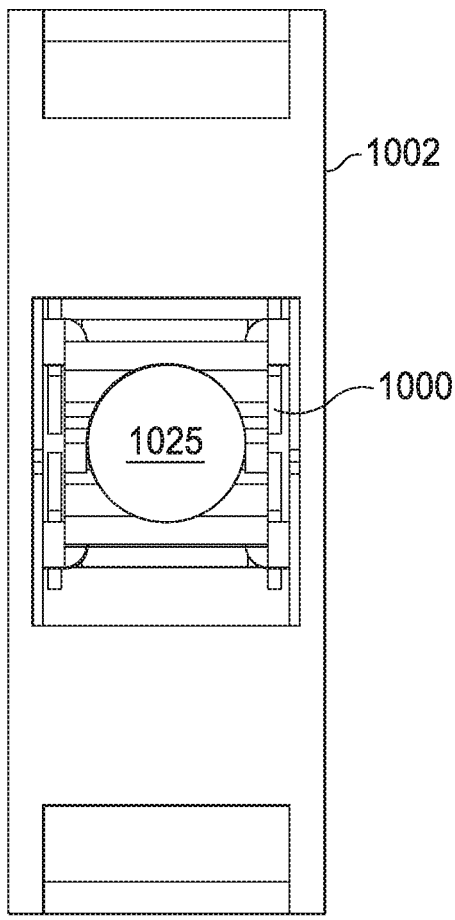
Figure 21E:
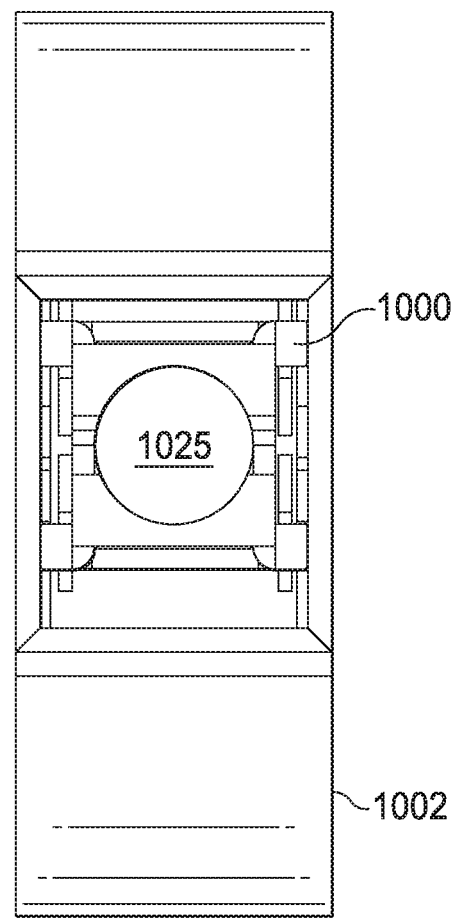

FIGS. 21A-21G illustrate various views of the exemplary linkage subset and the exemplary return assembly shown in FIG. 20. In particular, FIG. 21A illustrates another perspective view of the linkage subset and the return assembly. FIG. 21B illustrates the same perspective view as FIG. 21A of the linkage subset with a transparent view of the return assembly. FIG. 21C illustrates a front view of the linkage subset and a transparent view of the return assembly. FIG. 21D illustrates a right side view of the linkage subset and the return assembly. FIG. 21E illustrates a left side view of the linkage subset and the return assembly.

Figure 21F:
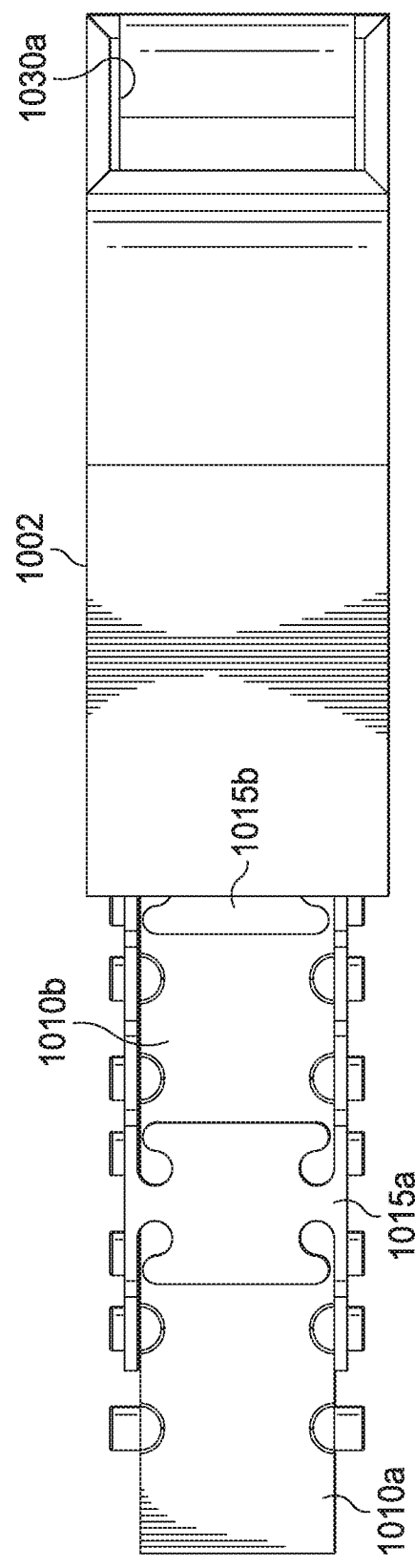
Figure 21G:
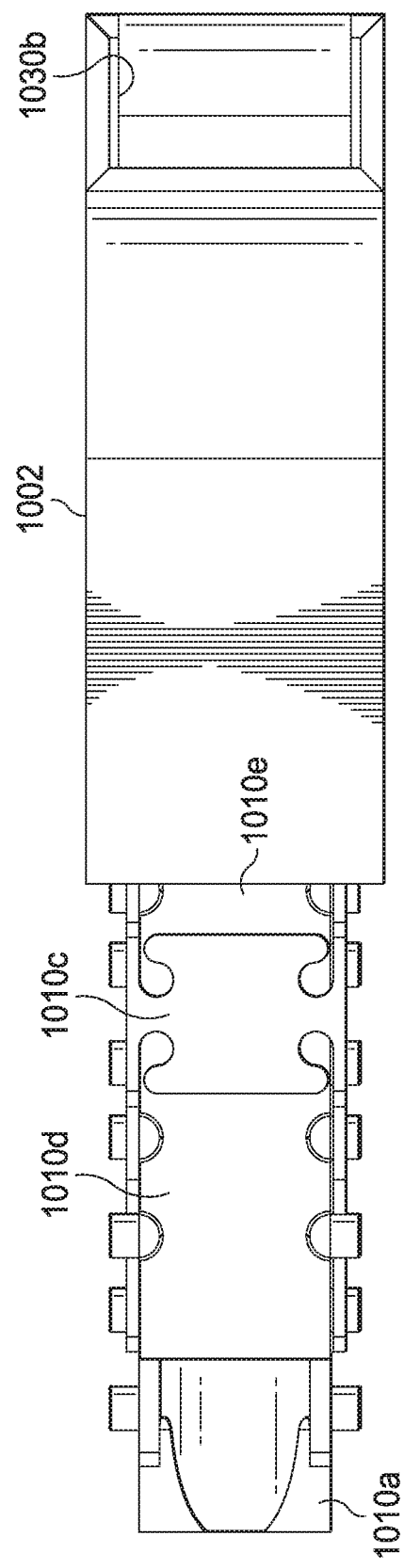

FIG. 21F illustrates a top view of the linkage subset and the return assembly. FIG. 21G illustrates a bottom view of the linkage subset and the return assembly.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
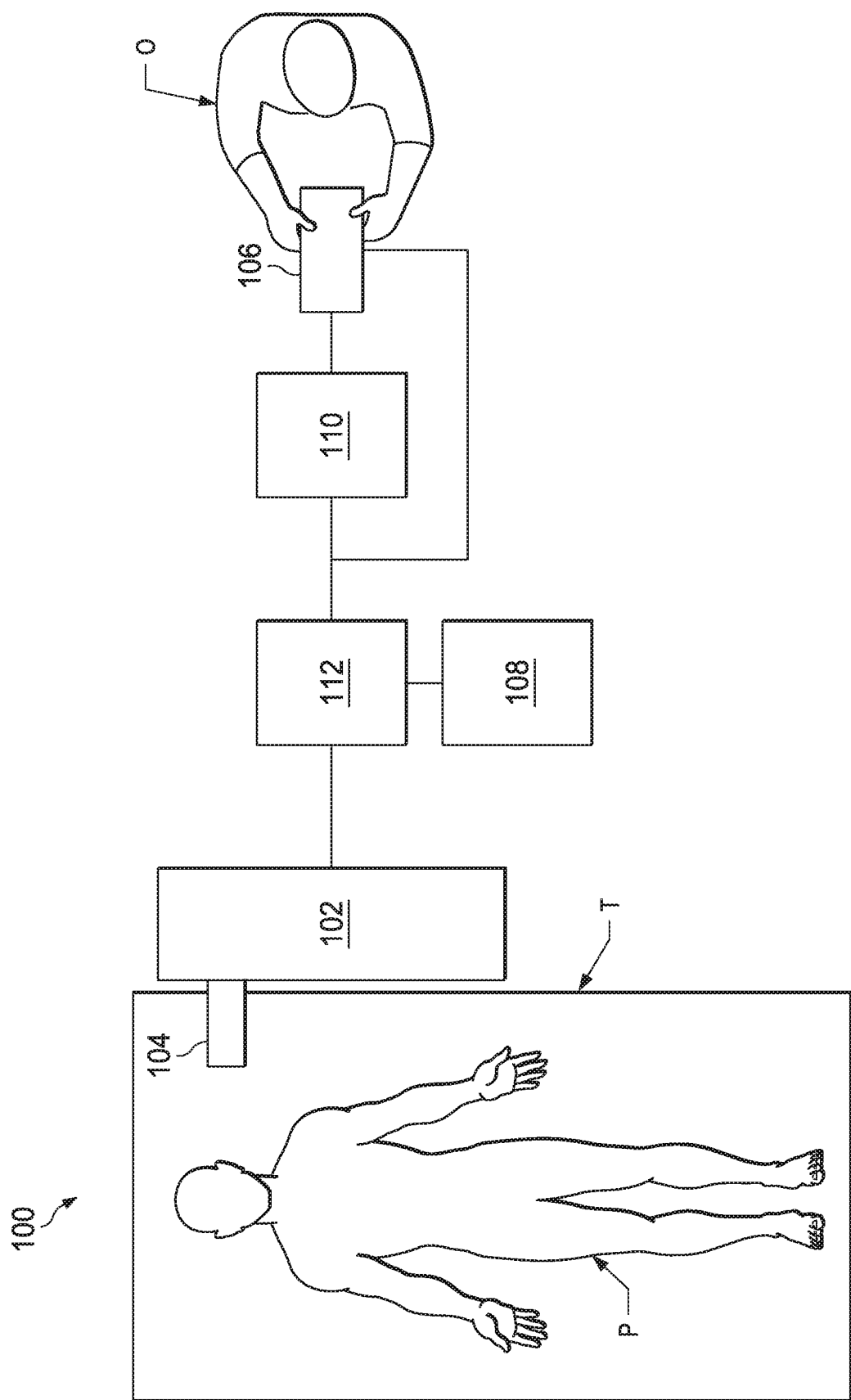
FIG. 1 is a simplified diagram of a teleoperated medical system, in accordance with embodiments of the present disclosure.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. As shown in FIG. 1, medical system 100 generally includes a teleoperational manipulator assembly 102 for operating a medical instrument 104 in performing various procedures on a patient P. Teleoperational manipulator assembly 102 is mounted to or near an operating table T. A master assembly 106 allows an operator O (e.g., a surgeon, a clinician, or a physician as illustrated in FIG. 1) to view the interventional site and to control teleoperational manipulator assembly 102.

Master assembly 106 may be located at a user's console which is usually located in the same room as operating table T, such as at the side of a surgical table on which patient P is located. However, it should be understood that operator O can be located in a different room or a completely different building from patient P. Master assembly 106 generally includes one or more control devices for controlling teleoperational manipulator assembly 102. The control devices may include any number of a variety of input devices, such as joysticks, trackballs, data gloves, trigger-guns, hand-operated controllers, voice recognition devices, body motion or presence sensors, and/or the like. To provide operator O a strong sense of directly controlling instruments 104 the control devices may be provided with the same degrees of freedom as the associated medical instrument 104. In this manner, the control devices provide operator O with telepresence or the perception that the control devices are integral with medical instruments 104.

In some embodiments, the control devices may have more or fewer degrees of freedom than the associated medical instrument 104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

The teleoperational assembly 102 supports the medical instrument system 104 and may include a kinematic structure of one or more non-servo controlled links (e.g., one or more links that may be manually positioned and locked in place, generally referred to as a set-up structure) and a teleoperational manipulator. The teleoperational assembly 102 includes plurality of actuators or motors that drive inputs on the medical instrument system 104 in response to commands from the control system (e.g., a control system 112). The motors include drive systems that when coupled to the medical instrument system 104 may advance the medical instrument into a naturally or surgically created anatomic orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like. Motor position sensors such as resolvers, encoders, potentiometers, and other mechanisms may provide sensor data to the teleoperational assembly describing the rotation and orientation of the motor shafts. This position sensor data may be used to determine motion of the objects manipulated by the motors.

The teleoperational medical system 100 also includes a sensor system 108 with one or more sub-systems for receiving information about the instruments of the teleoperational assembly. Such sub-systems may include a position/location sensor system (e.g., an electromagnetic (EM) sensor system); a shape sensor system for determining the position, orientation, speed, velocity, pose, and/or shape of the catheter tip and/or of one or more segments along a flexible body of instrument system 104; and/or a visualization system for capturing images from the distal end of the catheter system.

The visualization system (e.g., visualization system 231 of FIG. 2A) may include a viewing scope assembly that records a concurrent or real-time image of the surgical site and provides the image to the operator O, clinician, or surgeon. The concurrent image may be, for example, a two or three dimensional image captured by an endoscope positioned within the surgical site. In this embodiment, the visualization system includes endoscopic components that may be integrally or removably coupled to the medical instrument 104. However in alternative embodiments, a separate endoscope, attached to a separate manipulator assembly may be used with the medical instrument to image the surgical site. The visualization system may be implemented as hardware, firmware, software or a combination thereof which interact with or are otherwise executed by one or more computer processors, which may include the processors of a control system 112 (described below). The processors of the control system 112 may execute instructions comprising instruction corresponding to processes disclosed herein.

The teleoperational medical system 100 also includes a display system 110 for displaying an image or representation of the surgical site and medical instrument system(s) 104 generated by sub-systems of the sensor system 108. The display system 110 and the operator O input system 106 may be oriented so the operator O can control the medical instrument system 104 and the operator O input system 106 with the perception of telepresence.

The display system 110 may also display an image of the surgical site and medical instruments captured by the visualization system. The display system 110 and the control devices may be oriented such that the relative positions of the imaging device in the scope assembly and the medical instruments are similar to the relative positions of the operator's eyes and hands so the operator O can manipulate the medical instrument 104 and the hand control as if viewing the workspace in substantially true presence. By true presence, it is meant that the presentation of an image is a true perspective image simulating the viewpoint of an operator O that is physically manipulating the instrument 104.

Alternatively or additionally, the display system 110 may present images of the surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image data may be presented as two-dimensional, three-dimensional, or four-dimensional (including e.g., time based or velocity based information) images or as images from models created from the pre-operative or intra-operative image data sets.

In some embodiments often for purposes of imaged guided surgical procedures, the display system 110 may display a virtual navigational image in which the actual location of the medical instrument 104 is registered (i.e., dynamically referenced) with the preoperative or concurrent images/model to present the clinician or operator O with a virtual image of the internal surgical site from the viewpoint of the location of the tip of the instrument 104. In some examples, the viewpoint may be from a tip of medical instrument 104. An image of the tip of the instrument 104 or other graphical or alphanumeric indicators may be superimposed on the virtual image to assist the operatorcontrolling the medical instrument. Alternatively, the instrument 104 may not be visible in the virtual image.

In other embodiments, the display system 110 may display a virtual navigational image in which the actual location of the medical instrument is registered with preoperative or concurrent images to present the clinician or operator O with a virtual image of medical instrument within the surgical site from an external viewpoint. An image of a portion of the medical instrument or other graphical or alphanumeric indicators may be superimposed on the virtual image to assist the operatorcontrolling the instrument 104. As described herein, visual representations of data points may be rendered to the display system 110. For example, measured data points, moved data points, registered data points, and other data points described herein may be displayed on the display system 110 in a visual representation. The data points may be visually represented in a user interface by a plurality of points or dots on the display or as a rendered model, such as a mesh or wire model created based on the set of data points. In some embodiments, a visual representation may be refreshed in the display system 110 after each processing operations has been implemented to alter the data points.

The teleoperational medical system 100 also includes a control system 112. The control system 112 includes at least one memory and at least one computer processor (not shown), and typically a plurality of processors, for effecting control between the medical instrument system 104, the operator input system 106, the sensor system 108, and the display system 110. The control system 112 also includes programmed instructions (e.g., a non-transitory machine-readable medium storing the instructions) to implement some or all of the methods described in accordance with aspects disclosed herein, including instructions for providing pathological information to the display system 110. While control system 112 is shown as a single block in the simplified schematic of FIG. 1, the system may include two or more data processing circuits with one portion of the processing optionally being performed on or adjacent the teleoperational assembly 102, another portion of the processing being performed at the operator input system 106, another portion of the processing being performed at master assembly 106, and the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of teleoperational manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, teleoperational manipulator assembly 102. In some embodiments, the one or more actuators and teleoperational manipulator assembly 102 are provided as part of a teleoperational cart positioned adjacent to patient P and operating table T.

The control system 112 may further include a virtual visualization system to provide navigation assistance to operator O when controlling the medical instrument system(s) 104 during an image-guided surgical procedure. Virtual navigation using the virtual visualization system is based upon reference to the acquired preoperative or intra-operative dataset of the anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software, which may be used in combination with manual inputs is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the anatomy of patient P. The location can be used to produce both macro-level (external) tracking images of the anatomy of patient P and virtual internal images of the anatomy of patient P. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system.

The teleoperational medical system 100 may further include optional operation and support systems (not shown) such as illumination systems, steering control systems, irrigation systems, and/or suction systems. In some embodiments, the teleoperational system may include more than one teleoperational assembly and/or more than one master assembly. The exact number of manipulator assemblies will depend on the surgical procedure and the space constraints within the operating room, among other factors. Master assembly 106 may be collocated or they may be positioned in separate locations. Multiple master assemblies allow more than one operator to control one or more teleoperational manipulator assemblies in various combinations.

FIG. 2A is a simplified diagram of a medical instrument system 200 according to some embodiments. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally medical instrument system 200 may be used to gather (i.e., measure) a set of data points corresponding to locations within anatomic passageways of a patient, such as patient P.

The instrument system 200 includes an elongate device 202 (e.g., a catheter system) coupled to a drive unit 204. The elongate device 202 includes an elongated flexible body 216 having a proximal end 217 and a distal end or tip portion 218. In one embodiment, the flexible body 216 has an approximately 3 mm outer diameter. Other flexible body outer diameters may be larger or smaller. The catheter system 202 may optionally include a shape sensor 222 for determining the position, orientation, speed, velocity, pose, and/or shape of the catheter tip at distal end 218 and/or of one or more segments 224 along the body 216. The entire length of the body 216, between the distal end 218 and the proximal end 217, may be effectively divided into the segments 224. If the instrument system 200 is a medical instrument system 104 of a teleoperational medical system 100, the shape sensor 222 may be a component of the sensor system 108. If the instrument system 200 is manually operated or otherwise used for non-teleoperational procedures, the shape sensor 222 may be coupled to a tracking system 230 that interrogates the shape sensor and processes the received shape data.

Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below. The entire length of flexible body 216, between distal end 218 and proximal end 217, may be effectively divided into segments 224. If medical instrument system 200 is consistent with medical instrument 104 of a teleoperated medical system 100, tracking system 230. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 µm. In other embodiments, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering.

In some embodiments, the shape of the elongate device may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may be a component of an EM sensor system with positional sensor system 220 including one or more conductive coils that may be subjected to an externally generated electromagnetic field. Each coil of EM sensor system 220 then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X. Y. Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors in position sensor 220 may be positioned along flexible body 216 and then used for shape sensing. In some examples, a history of data from one or more of these sensors taken during a procedure may be used to represent the shape of elongate device 202, particularly if an anatomic passageway is generally static.

Flexible body 216 includes a channel 221 sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical instrument 226 is a biopsy instrument, which may be used to remove sample tissue or a sampling of cells from a target anatomic location. Medical instrument 226 may be used with an image capture probe also within flexible body 216. In various embodiments, medical instrument 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture instrument may be a fiber-optic bundle, such as a fiberscope, that couples to visualization system 231. The image capture instrument may be single or multi-spectral, for example capturing image data in one or more of the visible, infrared, and/or ultraviolet spectrums. Alternatively, medical instrument 226 may itself be the image capture probe. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably the bend distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable elongate devices are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the operator or other user with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing. "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, teleoperational manipulator assembly 102 of FIG. 1 may be replaced by direct operator control. In some examples, the direct operator control may include various handles and operator interfaces for hand-held operation of the instrument.

When using a teleoperational assembly to insert an instrument catheter into a patient anatomy, the outstretched catheter should be supported as the catheter is advanced into the patient. Otherwise, as the catheter is pushed from a proximal end and encounters friction in the patient anatomy at the distal end, the catheter may buckle or bend. To prevent this deformation of the catheter, an instrument guiding apparatus, as described herein, may be used to provide relatively rigid support to the catheter until it enters the patient anatomy. As the catheter enters the patient anatomy, the effective length of guiding apparatus decreases as portions of the apparatus fold away from or "unzip" along the catheter and move to an unobtrusive location. In some embodiments, the guiding apparatus feeds into a storage device as it "unzips" or disengages from the catheter. Thus, because the effective length of the guiding apparatus varies with the position of the catheter relative to the patient, the maximum length of the catheter may be used for patient treatment.

FIG. 3 illustrates an instrument interface portion 300 of a teleoperational manipulator assembly (e.g. teleoperational manipulator assembly 102) and an instrument guiding apparatus 302 according to an embodiment of the present invention. The instrument interface portion 300 includes drive inputs 304 to provide mechanical coupling of the instrument end effector and flexible body steering mechanism to the drive motors mounted to the teleoperational manipulator. For example, a pair of drive inputs may control the pitch motion of the distal end of the instrument flexible body, with one adaptor of the pair controlling motion in the upward direction and the other of the pair controlling motion in the opposite downward direction. Other pairs of drive inputs may provide opposing motion in other degrees of freedom for the flexible body and/or the end effector. Instrument interfacing with teleoperational or robotic manipulators is described, for example in U.S. Pat. No. 6,331,181, filed Oct. 15, 1999, disclosing "Surgical Robotic Tools, Data Architecture, And Use" and U.S. Pat. No. 6,491,701, filed Jan. 12, 2001 disclosing "Mechanical Actuator Interface System For Robotic Surgical Tools" which are both incorporated by reference herein in their entirety. The instrument interface portion 300 may also control instrument insertion by moving linearly along an insertion axis A.

The instrument guiding apparatus 302 has a distal end 301 and a proximal end 303. The instrument guiding apparatus 302 includes a variable-length support assembly 306 and a mounting strut 307 for coupling the instrument interface portion 300 to the assembly 306. In the pictured embodiment, the instrument guiding apparatus 302 includes a return assembly 308. In some embodiments, the variable-length support assembly 306 collapses or folds into the return assembly 308 as the instrument interface portion 300 advances toward the patient, thereby applying a linear force to the variable-length support assembly 306 in the direction of arrow A1 along the axis A.

The distal end 301 of the instrument guiding apparatus 302 is shown in detail in FIG. 4 in an initial configuration. The variable-length support assembly 306 includes a plurality of linkages 310 connected in series by hinge components 312. In some embodiments, the linkages 310 may be arranged in subsets of linkages that form a repeating pattern of linkages throughout the length of the variable-length support assembly 306. For example, in this embodiment, the linkages 310 are arranged in linkage subsets 314 that form a repeating pattern of linkages 310a, 310b, 310c, 310d, 310e. Individual linkages 310 and/or individual linkage subsets 314 may be substantially identical to one other, or may differ in size, shape, and/or material composition. In some embodiments, the hinge components 312 connect the adjacent linkages 310 in a spiral fashion, as described in further detail below with reference to FIGS. 5 and 6A-6D. In other embodiments, as described below with respect to FIGS. 16A-16E, 18, and 19A-19C, the hinge components 312 connect the adjacent linkages 310 in a more linear fashion. The hinge components 312 allow for movement between the linkages 310 in one or more degrees of freedom. In some embodiments, for example, the hinge components may allow for linear translation as well as rotational movement between the linkages 310. In the pictured embodiment, the return assembly 308 is coupled to the proximal-most linkages 310 of the variable-length support assembly 306, and a coupling element 309 links the return assembly 308 proximal-most linkages 310 of the variable-length support assembly 306 to the mounting strut 307. In the pictured embodiment, the elongated support assembly includes a stabilizing element 311, which may be used to stabilize the elongated support assembly relative to the operating field. Other embodiments may lack the stabilizing element 311.

As shown in FIG. 4, the variable-length support assembly 306 includes a central channel or lumen 315. The linkages 310 are connected and configured to allow the passage of a medical instrument such as, by way of non-limiting example, a catheter, through the central lumen 315. In the pictured embodiment, the central lumen 315 of the variable-length support assembly 306 is continuous with a central lumen 317 of the return assembly 308. Both central lumens 315 and 317 are sized and shaped to allow for the passage of a medical instrument such as, by way of non-limiting example, a catheter, through both the variable-length support assembly 306 and the return assembly 308.

FIGS. 5A-5B and 6A-6H illustrate various views of a linkage subset 320, which is an exemplary linkage subset 314 of the variable-length support assembly 306 described above with reference to FIG. 4 according to one embodiment of the present disclosure. FIG. 5A illustrates a perspective view of the linkage subset 320, and FIG. 5B illustrates a more detailed perspective view of the linkages 310c-310e shown in FIG. 5A. FIG. 6A illustrates a front view of the linkage subset 320. FIG. 6B illustrates a back view of the linkage subset 320. FIG. 6C illustrates a right side view of the linkage subset 320. FIG. 6D illustrates a left side view of the linkage subset 320. FIG. 6E illustrates a top view of the linkage subset 320. FIG. 6F illustrates a bottom view of the linkage subset 320. FIGS. 6G and 6H illustrate front, partially transparent views of the linkage subset 320.

The linkage subset 320 comprises five individual linkages 310a, 310b, 310c, 310d, and 310e aligned around a central axis CA. Each linkage 310a-e is coupled to adjacent linkages in series. For example, the linkage 310a is coupled to the linkage 310b, the linkage 310b is coupled to the linkages 310c and 310a, the linkage 310c is coupled to the linkages 310d and 310c, and the linkage 310d is coupled to the linkages 310e and 310c. In FIGS. 5 and 6A-6F, the linkage subset 320 is shown in a partially "unzipped" or inactive configuration, with the linkage 310e outwardly rotated in the direction of arrow AA about a vertical axis VA. In contrast, the linkage subset 320 is shown in a "zipped" or active configuration in FIGS. 9A, 9B, and 12A, with each linkage 310a-e snugly coupled to the adjacent linkage and rotated inward in the direction of arrow A2 toward the central axis CA.

As shown in FIGS. 5A, 5B, and 6A-6D, in the pictured embodiment, each linkage 310a-e is shaped as an irregular hemi-cylinder with a convex outer surface 325a-e and a concave inner surface 330a-e, respectively. In other embodiments, each linkage may be shaped as any type of partial cylinder (i.e., any fraction of a cylinder cut along its axial length). The linkages 310a-e each include a first recess 335a-e and second recess 340a-e on the inner surfaces 330a-e, respectively. In FIGS. 5A and 5B, the linkage 310e is shown rotated outwardly from the central axis CA, revealing the first recess 335e and the second recess 340e of the linkage 310e.

In the pictured embodiment, the linkages 310a-e are identical to one another in shape and size. In other embodiments, the individual linkages 310a-e may differ in shape and/or size from one another. Before further describing how the linkages 310a-e interact with one another to form a portion (i.e., the linkage subset 314) of the variable-length support assembly 306 described above with reference to FIG. 4, an individual linkage will be described. In particular, the linkage 310d is illustrated in detail in FIGS. 7A-7F. FIG. 7A illustrates a front view of the linkage 310d. FIG. 7B illustrates a back view of the linkage 310d. FIG. 7C illustrates a right side view of the linkage 310d. FIG. 7D illustrates a left side view of the linkage 310d. FIG. 7E illustrates a top view of the linkage 310d. FIG. 7F illustrates a bottom view of the linkage 310d.

The linkage 310d includes a projection 345d and a body portion 350d. The body portion 350d extends from an upper surface 352d to a lower surface 354d. In the pictured embodiment, the upper surface 352d and the lower surface 354d share matching angles of curvatures or slope profiles. Thus, the upper and lower surfaces 352, 354 of both immediately adjacent and non-adjacent linkages 310 can smoothly meet and rest against one another as the linkages 310 spiral into an active or "zipped up" configuration. For example, when the linkage 320 is in a "zipped" or active configuration, the upper surface 352d of the linkage 310d contacts the lower surface 352a of the linkage 310a as well as the lower surface 352b of the linkage 310b. The upper and lower surfaces 352d, 354d may be generally planar abutment surfaces and/or may include keyed features for interconnection with mating features of an adjacent linkage 310.

As described above, FIGS. 6G and 6H illustrate front, partially transparent views of the linkage subset 320 that allows better visualization of how the linkages 310 interact with one another. In particular, FIG. 6G illustrates a front view of the linkage subset 320 with a transparent view of the linkage 310c. FIG. 6H illustrates a front view of the linkage subset 320 with a transparent view of the linkage 310d. The body portion 350d of the linkage 310d includes a first recess 335d upon the inner surface 330d, which is sized and shaped to receive the projection 345 of a serially connected, non-adjacent linkage (i.e., the projection 345a of the linkage 310a, as shown in FIG. 6A and FIG. 6G). The body portion 350d also includes a second recess 340d upon the inner surface 330d, which is sized and shaped to receive the projection 345 of a serially connected, adjacent linkage (i.e. the projection 345b of the linkage 310b, as shown in FIGS. 6B and 6H).

Referring back to FIG. 5B, the pictured embodiment illustrates the interaction between the linkages 310c. 310d, and 310e. In particular, the body portion 350e includes a first recess 335e, which is sized and shaped to receive a projection 345b of the serially connected, nonadjacent linkage 310b. The body portion 350e also includes a second recess 340e, which is sized and shaped to receive the projection 345c of a serially connected, nonadjacent linkage 310c. Thus, when the linkage subset 320 is in a "zipped" or active configuration, the projections 345 of the individual linkages 310 nest within the recesses 335, 340 of neighboring linkages, thereby releasably "locking" the linkages 310 together and enhancing the structural stability of the variable-length support assembly 306. The projections 345 and recesses 335, 340 allow the linkages 310 to function in a similar manner to the teeth of a zipper, with each linkage 310 locking another linkage 310 into place in the variable-length support assembly 306 while preserving a channel within which the medical instrument may travel.

As indicated by FIGS. 6E and 6F, when the linkage subset 320 is in a "zipped" or active configuration, the inner surfaces 330 of the linkages 310 form a generally continuous, cylindrical lumen 355. The lumens 355 of several linkage subsets (e.g., the linkage subsets 314) combine to form the central lumen 315 of the variable-length support assembly 306 shown in FIG. 4.

Each linkage 310 in the linkage subset 320 is connected to the two adjacent linkages via pivot pins 342, 344 (not shown) that extend through the body portion 350. In this embodiment, the pivot pins 410 act as the hinge components 312 shown in FIG. 4. The pivot pins 342, 344 allow for both translational movement between the linkages 310 along the central axis and rotational movement between the linkages 310 about the pivot pins 342 (for example, in the direction of arrow AA in FIG. 5 and arrow A2 in FIG. 9A). For example, a first pivot pin 342 (not shown) extends from within an upper channel 360d in the body portion 350d into a lower channel 365c (not shown in FIGS. 7A-7F) of the adjacent linkage 310c, thus hingedly coupling the adjacent linkages. Similarly, a second pivot pin 344 (not shown) extends from within a lower channel 370d into an upper channel 360e (not shown in FIGS. 7A-7F) of the adjacent linkage 310e, thus hingedly coupling the adjacent linkages. The pivot pins 342, 344 operate in a manner similar to the pivot pins 410 described below with reference to FIGS. 8A and 8B.

In the embodiments pictured herein, the linkages 310a-c and 310e of the linkage subset 320 are identical in shape and size to the linkage 310d described above with reference to FIGS. 7A-7F. The linkages 310a-e may be formed of any of a variety of rigid or semi-rigid materials including metals, polymers, or rubber. In various alternative embodiments, the linkage subsets 314 may have fewer or more than five linkages. Within each linkage subset 320, each linkage 310a-e has individual upper channels 360a-e, lower channels 365a-e, curved upper surfaces 352a-e, and lower surfaces 354a-e.

FIGS. 8A and 8B illustrate exemplary linkage subsets 400 of an instrument guiding apparatus according to an embodiment of the present disclosure. FIG. 8A illustrates the exemplary linkage subset 400 in a splayed and compact configuration. FIG. 8B illustrates exemplary linkage subsets 400 in a splayed and expanded configuration. The linkage subset 400 is substantially similar to the linkage subset 320 described above except as described below. In particular, the linkage subset 400 includes at least nine linkages 405 coupled by pivot pins 410. The linkages 405 are substantially similar to the linkages 310 described above. FIGS. 8A and 8B illustrate the translational movement between the linkages 405 enabled by the pivot pins 410.

In FIG. 8A, the linkages 405 are in a compact configuration, with an upper surface 412 of each linkage 405 positioned as far apart from the neighboring upper surface 412 as the pivot pins 410 would allow. As shown in FIG. 8A, the pivot pins 410 are partially exposed, extending from upper channels 415 and lower channels 420 within the linkages 405. If force is applied upon the linkages 405 in the direction of the upper surfaces 412, as indicated by the arrow A3, the linkages 405 slide in the same direction upon the pivot pins 410 to reveal the pivot pins 410 and assume a compact, "unzipped," and splayed or inactive configuration.

In FIG. 8B, the linkages 405 are shown in an expanded configuration, with the upper surface 412 of each linkage 405 positioned adjacent to the neighboring upper surface 412 to create a generally continuous line of upper surfaces 412 indicated by the dotted line. In FIG. 8B, the linkages 405 are shown slid apart from one another along the pivot pins 410 such that the pivot pins 410 are largely positioned with the upper channels 415 and the lower channels 420. If force is applied on the linkages 405 in the direction of projections 425, as indicated by the arrow A4 (e.g., in the opposite direction of the arrow A3 shown in FIG. 8A), then the linkages 405 slide apart from one another along the pivot pins 410, sheathing the pivot pins 410 within the upper channels 415 and lower channels 420 of the linkages 405. Thus, as the linkages 310 of the variable-length support assembly 306 "zip" or "unzip," the linkages 310 both pivot and slide along the pivot pins 410 to lock and unlock from one another.

FIGS. 9A and 9B illustrate the linkage subset 320 in a "zipped" or active configuration. In particular, FIG. 9A illustrates a partially transparent perspective view of the linkage subset 320 in a "zipped" or active configuration, and FIG. 9B illustrates a top view of the linkage subset 320 in an elongated "zipped" or active configuration. The linkages 310a-e are shaped and sized such that when serially assembled in such a "zipped" or active configuration, the convex outer surfaces 325a-e form a generally continuous outer surface of the cylindrical variable-length support assembly 306. When several linkage subsets 320 are interlocked in such a "zipped" or active configuration, the inner surfaces 330a-e of each of the linkages 310 are aligned such that the channels 335 of each of the linkage subsets 320 are linearly aligned generally along the insertion axis A to form the continuous central lumen 315 extending through the variable-length support assembly 306 shown in FIG. 4. In other alternative embodiments, the diameter of the channels 335 of the linkage subsets 320 may be sized to accommodate different diameter catheters. In still other alternative embodiments, the diameter of the channels 335 of different linkage subsets may vary along the length of the variable-length support assembly 306 to match the diameter of a catheter with a diameter varying along its length.

FIG. 10 illustrates a detailed view of an exemplary linkage subset 320' according to one embodiment of the present disclosure. The linkage subset 320' includes at least the linkages 310c', 310d', and 310e'. The linkages 310c', 310d', and 310e' are substantially identical to the linkages 310c, 310d, and 310e described above except for the differences described herein. Although the linkages 310 in the embodiments described above exhibit a right-handed helical pattern of assembly into the "zipped" or active configuration, the linkages 310' of the linkage subset 320' exhibit a left-handed helical pattern of assembly into the "zipped" or active configuration.

FIG. 11 illustrates a schematic side view of the distal end of the instrument guiding apparatus 302 of FIG. 4 in a partially "unzipped" or inactive configuration according to an embodiment of the present invention. As the return assembly 308 is advanced distally toward the patient along the insertion axis A in the direction of the arrow A1, the return assembly 308 acts as an effective "zipper pull" that operates to "unzip" the variable-length support assembly 306 by nudging the proximal-most linkages 310 apart and into the return assembly 308.

FIG. 12 illustrates an interventional instrument 500 and the instrument guiding apparatus 302 of FIGS. 3 and 4 coupled to a teleoperational manipulator assembly 550 in a patient environment according to an embodiment of the present invention. The teleoperational manipulator assembly 550 includes the instrument interface portion 300. The instrument 500 is positioned in a surgical environment with a patient anatomy P. As shown in FIG. 12, the instrument system 500 includes an elongated flexible catheter 502 extending generally along the insertion axis A when the instrument system is coupled to the teleoperational interface portion 300. In operation, as illustrated in FIG. 12, movement of the instrument interface portion 300 distally along the axis A advances the mounting strut 307 which moves the proximal end 303 of the variable-length support assembly 306 distally (i.e. toward the patient anatomy P). As the proximal end 303 of the variable-length support assembly 306 is moved distally, the proximal-most linkages 310 slide toward one another along the axis A and "unzip" or unwind, with the individual linkages 310 nearest the return assembly 308 rotating outward from and sliding distally on the pivot pins 410 along the axis A before entering the return assembly 308. These outwardly rotated linkages 310 are directed to the return assembly 308, as illustrated in FIG. 11.

An opeartor may insert the catheter 502 into the central lumen 317 of the return assembly 308 and the central lumen 315 of the elongated support assembly (introduced in FIG. 4) to support the longitudinal length of the catheter 502 throughout the process of insertion into the patient anatomy P. Regardless of the angle of insertion, the catheter 502 is generally able to flex slightly to conform to the entry angle into the central lumens 315, 317. Inside the variable-length support assembly 306, the flexible catheter 502 returns to a generally straight configuration within the continuous central lumen 315 (which, as described above, is formed by the inner surfaces 330 of the linkages 310). As the instrument interface portion 300 is advanced, under the operator's control, distally along the insertion axis A, it also moves the catheter 502 and the proximal end 303 of the instrument guiding apparatus 302 distally. As the instrument interface portion 300 and the catheter 502 are advanced distally along the axis A toward the patient anatomy P, the variable-length support assembly 306 shortens as the proximal-most linkages 310 are "unzipped" and fed into the return assembly 308, as indicated by FIG. 11. At the proximal end 303 of the instrument guiding apparatus 302, the return assembly 308 incrementally separates the variable-length support assembly 306 into "unlocked" linkages 310 that routed into the return guide 308. As the proximal-most linkages 310 are directed into the return assembly 308, the catheter 502 continues to advance distally past the distal end 301 of the instrument guiding apparatus 302 for insertion into the patient anatomy P. As the variable-length support assembly 306 shortens in accord with the diminishing external portion of the catheter 502, the central lumen 315 remains continuous along the remaining "zipped-up" linkages. Thus, the flexible catheter 502 is continuously supported along its external length (i.e. the portion of the catheter 502 that has not yet entered the patient anatomy P) within the variable-length support assembly 306 as it enters the patient anatomy P. As the catheter 502 is removed from the patient anatomy P, the return assembly 308 moves in reverse, releasing the linkages 310 to support the withdrawn catheter 502. The released linkages 310 are biased to reassemble (i.e., slide proximally down the pivot pins 410 to allow the projections 345 to "lock" into the channels 340, 355) into the gradually lengthening interlocked variable-length support assembly 306.

As described above, the variable-length support assembly 306 can support the catheter 502 shown in FIG. 12 along its changing external (i.e., positioned outside the patient anatomy P) length as it enters or exits the patient anatomy P. With the linkages 310 interlocked along the insertion axis A, the support assembly 306 minimizes bending or buckling of the catheter 502 as the distal end of the catheter 502 is advanced into the patient anatomy P. Any significant bending or buckling of the catheter 502 may damage optical fibers used for shape sensing or endoscopy. Also, bending or buckling may make advancing the catheter non-intuitive, since the user will observe no distal tip movement even though the user is advancing the proximal end of the catheter. In the described embodiments, the linkages 310 form a self-supporting structure that requires no support rails or other rigid, elongated supports along the axis A. Thus, the proximal-most linkages 310 are able to move out of the path of the advancing teleoperational interface portion 300 by receding into the return assembly 308. As compared to a telescoping support assembly that includes linkages that circumferentially telescope into one another in a traditional manner, the variable-length support assemblies described herein support the entire exposed length of the catheter 502 as it advances proximally along the axis of insertion A.

FIGS. 13A-13C more clearly illustrate the mechanics of a variable-length support assembly as it "unzips" or assumes an inactive configuration to enter the return assembly 308. FIGS. 13A-13C illustrate side views of an exemplary variable-length support assembly 600 including the linkage subset 320 shown in FIG. 5A according to one embodiment of the present disclosure. In the pictured embodiment, the variable-length support assembly 600 includes at least two additional linkages 310' and 310". In FIGS. 13A and 13B, a catheter 605 extends through a central lumen 610 of the variable-length support assembly 600. In FIG. 13A, the variable-length support assembly 600 is in a "zipped" or active configuration, with each linkage 310 locked to an adjacent linkage 310 to form the central lumen 610. The catheter 605 can slide within the central lumen 610, but it remains in a relatively straight configuration within the lumen 610. When the linkages 310 are in a "zipped" or active configuration, the central lumen 610 has an initial length L1.

In FIG. 13B, the variable-length support assembly 600 is in a partially "unzipped" or inactive configuration, with the linkages 310c-e unwinding or "unzipping" from each other by rotating outward in the direction of arrow A4 and sliding upward in the direction of arrow A5 along the pivot pins (not shown). As a force F is applied on the variable-length support assembly 600 in the direction of the arrow A5, the linkages 310 are forced to slide in the direction of A5 and biased (e.g., by the curvature of the upper surfaces 352 and lower surfaces 354 of the linkages 310) to rotate outward in the direction of arrow A4 when the extent of the sliding movement is reached. The central lumen 610 now has a smaller length L2. Consequently, a shorter length of the catheter 605 is supported within the central lumen 610 because the length L2 of the central lumen is less than the original length L1 of the central lumen.

In FIG. 13C, the variable-length support assembly 600 is in an entirely "unzipped" or inactive configuration, with the linkages 310a-e, 310', and 310" unwound or "unzipped" from each other after rotating outward in the direction of arrow A4 and sliding upward in the direction of arrow A5 along the pivot pins (not shown). As shown in FIG. 13C, as the variable-length support assembly 600 unwinds or "unzips," the linkages 310 wind around one another to form a spiral shape resembling a nautilus shell.

FIG. 14 illustrates an exemplary return assembly 650 according to one embodiment of the present disclosure. As mentioned above with reference to FIG. 11, as the instrument interface portion 300 and the catheter 502 are advanced distally along the axis A toward the patient anatomy P, the variable-length support assembly 306 shortens as the proximal-most linkages 310 are "unzipped" and fed into the return assembly 308. In use with any of the variable-length support assemblies described above, the return assembly 650 would serve as a "zipper pull" traveling in the distal direction, nudging the proximal-most linkages to slide along the pivot pins 410 in the distal direction along the axis A before rotating outwards (i.e. "unzipping") to enter the return assembly 650. Similarly, if the return assembly 650 is moved in the proximal direction along the axis A, the linkages 310 would emerge from the return assembly 650, rotate inwards, and slide proximally along the pivot pins 410 until the linkages "locked" together once again and the variable-length support assembly 306 lengthened, regaining at least a partially "zipped" or active configuration.

In the pictured embodiment, the return assembly 650 is shaped as a hollow spiral resembling a nautilus shell. The shape and dimensions of the return assembly 650 are designed to complement the shape and dimensions of any one of the variable-length support assemblies described above. In particular, the return assembly 650 is sized and shaped to nudge the linkages 310 apart (e.g., to urge the proximal-most linkage 310 to slide distally and rotate outwardly on the pivot pin 410), to guide these linkages 310 into the return assembly 650, and to accommodate the linkages 310 in an "unzipped" configuration within a passageway 655. In the pictured embodiment, the passageway 655 is shaped as a spiral channel. In some embodiments, the return assembly includes an entrance and exit ramp 660 designed to facilitate and direct the smooth entry and exit of the linkages 310 from the passageway 655. The entrance and exit ramps 660 may be sized and shaped to direct the linkages 310 at a constant speed into the passageway 655 of the return assembly 650. In alternate embodiments, the steepness of the ramps 660 may be different from that shown in the pictured embodiment. In particular, the ramp steepness or angle may be altered to enable a shorter or more compact storage configuration (which may, however, cause higher friction of the linkages sliding on the ramp).

FIG. 15 is a flowchart 700 describing a method of guiding an interventional instrument (e.g., the instrument 500) using the instrument guiding apparatus 302. At 705, the method 700 includes receiving a catheter portion of an interventional instrument into an instrument guiding apparatus, and, in particular, into a variable-length support assembly. As described above, the catheter may be inserted into a continuous central lumen of the variable-length support assembly. In most instances, the variable-length support assembly is in a "zipped-up" or active configuration, with the adjacent linkages locked into one another along the length of the support assembly. At 710, the method 700 includes receiving an indication at the teleoperational control system that the interventional instrument system is coupled to the teleoperational manipulator. At 715, the method 700 includes advancing the interventional instrument system, including the return assembly, along the insertion axis A. At 720, the method 700 includes incrementally "unwinding" or "unzipping" the proximal end of the variable-length support assembly into individual linkages by applying force to the proximal end of the support assembly, thereby sliding the proximal-most linkages outward and distally along their pivot pins. As the variable-length support assembly is incrementally unzipped, the distal catheter portion of the interventional instrument is advanced distally into the patient anatomy. The proximal portion of the catheter remains supported by the interlocked, "zipped-up" distal portion of the variable-length support assembly. At 725, the method 700 includes sheathing the proximal-most linkages within the return assembly, thereby shortening the length of the variable-length support assembly as the catheter enters the patient anatomy.

FIGS. 16A-16G illustrate various views of an exemplary linkage subset 800. In particular. FIG. 16A illustrates a front view of the linkage subset 800. FIG. 6B illustrates a back view of the linkage subset 800. FIG. 16C illustrates a right side view of the linkage subset 800. FIG. 16D illustrates a left side view of the linkage subset 800. FIG. 16E illustrates a top view of the linkage subset 800. FIG. 16F illustrates a bottom view of the linkage subset 800. The linkage subset 800 is an example of the linkage subset 314 of the variable-length support assembly 306 described above with reference to FIG. 4 according to one embodiment of the present disclosure.

In the pictured embodiment, the linkage subset 800 comprises 11 individual linkages 805a-k serially coupled to one another. As illustrated by the linkages 805i-k in FIG. 16A, which are substantially identical to the other linkages 810a-h (except for alternating linkages 805 including two slots 807, 808 and an aperture 809), each linkage 805 is shaped as a relatively flat tab including two hinge tips 810 at one end and two hinge pins 815 at the opposing end. The linkage 805j includes a body portion 820j integrally and rigidly connected to a flange portion 825j. The flat and generally rectangular shape of the body portions 820 and the arcuate shape of the flange portions 825 should not be considered a limiting feature, as other shapes and configurations of the linkages are contemplated for other embodiments of the present invention. These may include, for example, round, rectangular, oblong, elliptical, triangular, and square shapes. The hinge tips 810 of each linkage 805 are shaped and sized to interact with the hinge pins 815 of an adjacent linkage 805 to create a hinge mechanism that pivotally connects adjacent linkages 805.

When assembled into an elongated support assembly 306, each alternating linkage 805 includes two slots 807, 808 and the aperture 809 within the body portion 820. For example, in the illustrated embodiment of FIG. 16A, the linkages 805a, 805b, 805h, 805f, and 805k each include two slots 807 and the aperture 809. The slots 807 are shaped and sized to receive individual flange portions 825 of other linkages 805 when the linkage subset 800 is in an active or "zipped-up" configuration. The apertures 809 are shaped and sized to receive individual hinge mechanisms of other linkages 805 when the linkage subset 800 is in an active or "zipped-up" configuration. FIGS. 16A-16G show the linkages 805a-h assembled together in an active or "zipped up" configuration, with the flange portions 825a-h positioned within the appropriate slots 807 and 808. For example, FIG. 16A illustrates the upper slot 807b receiving the flange portion 825a and the lower slot 808b receiving the flange portion 825e.

As best shown by the top and bottom views of the linkage subset 800 illustrated in FIGS. 16F and 16G, the linkage subset 800 is formed of four strips of linkages 805 that are connected at right angles to form a central lumen 830. Each strip of linkages 805 forms a support member. The central lumen 830 corresponds to the central lumen 315 described above with reference to FIG. 4.

As best illustrated by the linkages 805i-k in FIGS. 16B and 16C, alternating linkages 805 are coupled to each other via the hinge mechanisms, i.e., the hinge pins 815 connect to the hinge tips 810. Moreover, the adjacent linkages 805 are reversed or flipped such that the hinge tips 810 of adjacent linkages face in opposite directions, thus creating an accordion-like structure, as shown in FIG. 17. FIG. 17 is a schematic diagram of the unfolding and folding mechanism of the linkage subset 800 illustrated in FIGS. 16A-16G as it transitions between an active and an inactive configuration. In particular, FIG. 17 illustrates a diagrammatic cross-section of the linkage subset 800 through the lines A-A shown in FIG. 16G. Unlike the linkages 310 described above with reference to FIGS. 5A-7F, the linkages 805 are not slidable relative to one another. Instead, the linkages 805 are configured to swivel approximately 180 degrees at the hinge mechanisms (i.e. the hinge pins 815 and hinge tips 810) to fold in an accordion-like manner from an extended, "zipped," and active configuration 830 into a more compact, "unzipped," and inactive configuration 840. Alternating linkages 805 fold in opposite directions. For example, with reference to FIG. 16C, the linkage 805i swivels about the hinge pin 815i in the direction of an arrow A6 while the linkage 805j folds about the hinge pin 815j in the direction of an arrow A5. In the more compact configuration (e.g., the configuration 840 shown in FIG. 17), a first surface 842i of the linkage 805i rests against a second surface 844j of the linkage 805j, and a first surface 842j of the linkage 805j rests against a second surface 844k of the linkage 805k. Referring back to the "zipped" linkage subset 800 shown in FIG. 16B-16F, the linkage subset 800 unzips into four distinct, vertically-staggered strips of linkages 805. Just as each car at a four-way stop moves sequentially and independently of one another, the distal-most linkage 805 of each strip of linkages folds independently of each other and in sequence, with the linkages 805 folding down in a spiral in the direction of arrow S1 in FIG. 16F. For example, after the linkage 805i folds, the linkage 805a folds, and then the linkage 805b folds, and then the linkage 805c folds. Each time, the folding linkage 805 either locks or unlocks on features (e.g., slot 807 or 808 may capture the flange portion 825) of its neighboring or adjacent linkage 805.

FIG. 18 illustrates a perspective view of an exemplary linkage subset 900. FIGS. 19A-19E illustrate various views of the exemplary linkage subset 900 coupled to an exemplary return assembly 902. In particular, FIG. 19A illustrates a front, partially transparent view of the linkage subset 900 and the return assembly 902. FIG. 19B illustrates a back view of the linkage subset 900 and the return assembly 902. FIG. 19C illustrates a right side view of the linkage subset 900 and the return assembly 902. FIG. 19D illustrates a top view of the linkage subset 900 and the return assembly 902. FIG. 19E illustrates a bottom view of the linkage subset 900 and the return assembly 902.

The linkage subset 900 is an example of the linkage subset 314 of the variable-length support assembly 306 described above with reference to FIG. 4 according to one embodiment of the present disclosure. The linkage subset 900 comprises several individual linkages 910 coupled to one another to form a portion of a variable-length support assembly. In the pictured embodiment, only the linkages 910a-p are visible, although additional linkages are present in the linkage subset 900. Each of the linkages 910 is substantially identical to one another, and each linkage 910 is shaped as a relatively flat, oblong tab including an aperture 912, a projection 914, a flange 916, and multiple slots 918. The flat and generally oblong shape of the linkages 910 and the rounded shapes of the apertures 912 and projections 914 should not be considered a limiting feature, as other shapes and configurations are contemplated for other embodiments of the present invention. These may include, for example, round, rectangular, oblong, elliptical, triangular, and square shapes.

For the sake of simplicity, only the linkage 910m is described in more detail. It is to be understood that the linkages 910 are substantially identical. In the pictured embodiment, the linkage 910m includes an aperture 912m at one end and a projection 914m at the opposing end. The aperture 912 may have any shape that corresponds to the projection 914 of the adjacent linkage, enabling the projection 914 of one linkage to moveably couple to the aperture 912 of an adjacent linkage. In the pictured embodiment, both the apertures 912 and the projections 914 have a rounded shape. The projection 914k is moveably coupled to the aperture 912m. The projections 914 of each linkage 910 are shaped and sized to interact with the apertures 912 of a serially connected linkage 910 to create a hinge mechanism that pivotally connects adjacent linkages 910. Thus, the apertures 912 receive individual projections 914 of serially linked linkages 910 whether the linkage subset 900 is in an active or "zipped-up" configuration or in an inactive or "un-zipped" configuration. The projections 914 are always coupled to the apertures 912 to create at least four elongated strips of linkages 910 that interact to form the linkage subset 900.

The linkage 910m also includes two slots 918m and a flange 916m. The slots 918 are shaped and sized to receive individual flange portions 916 of other linkages 910 when the linkage subset 900 is in an active or "zipped-up" configuration. FIGS. 18 and 19A-19C show the linkages 910 assembled together in an active or "zipped up" configuration, with the flange portions 916 positioned within the corresponding slots 918.

As best shown by the top and bottom views of the linkage subset 900 illustrated in FIGS. 19D and 19E, the linkage subset 900 is formed of four interlocking strips or support members of serially connected linkages 910 that are interlocked together at the general midline of each strip to form a central lumen 920. The slots 918 receive the flanges 916 of nearby linkages 910, thereby allowing serially connected rows of linkages 910 to rest snugly against one another at approximately right angles to form the central lumen 920. The central lumen 920 corresponds to the central lumen 315 described above with reference to FIG. 4. In the pictured embodiment, the linkage subset 900 includes a distal cap 922 upon which the distal-most linkages are anchored. Other embodiments may lack such an endcap. As the individual strips of linkages unzip or unlock, the linkages 910 of each strip swing one-by-one into place as the protruding arm is locked into place by the neighboring linkage's slot (the slot of linkage to the right, for example). As the strips unzip, the unzipped linkages 910 of each individual strip are coiled into a helix into canisters, as described further below.

Returning to FIG. 19A, the return assembly 902 comprises four cylindrical canisters 924*a-d* that are linked together but capable of independent rotation about central bars 926*a-d*, respectively. As shown in FIG. 19A, as the linkage subset 900 "unzips" or transitions from an expanded, "zipped" configuration into a more compact, "unzipped" configuration (i.e. as the return assembly 902 advances in a distal direction down the linkage subset 900), the individual strips or support members of serially-connected linkages 910 wind around the central bars 926*a-d* and into the canisters 924*a-d*, thereby shortening the length of the variable-length support assembly of which the linkage subset 900 is a part. The unzipping of the linkage strips occurs asynchronously in the sense each linkage of a strip becomes unlocked or decoupled from the linkage of an adjacent strip in a one-at-a-time, serial progression. In this example, each linear support member or strip of linkages 910 winds into a separate canister 924*a-d*. For example, in FIG. 19A, the linkages 910*b*, 910*e*, 910*h*, 910*o*, 910*k*, and 910*m* form a single support member or strip of linkages that is shown winding into the canister 924*a* of the return assembly 902 about the central bar 926*a* in the direction of arrow A7. Unlike the linkages 310 described above with reference to FIGS. 5A-7F, the linkages 910 are not slidable relative to one another. Instead, the linkages 910 are configured to rotate at the hinge mechanisms created by the projections 914 and the apertures 912 to unlock and wind from an extended, "zipped," and active configuration into a more compact. "unzipped," and inactive configuration (i.e., when at least some linkages 910 coil into the return assembly 902).

FIG. 20 illustrates a perspective view of an exemplary linkage subset 1000 coupled to an exemplary return assembly 1002. FIGS. 21A-21E illustrate various views of the exemplary linkage subset 1000 coupled to the exemplary return assembly 1002. In particular, FIG. 21A illustrates another perspective view of the linkage subset 1000 and the return assembly 1002. FIG. 21B illustrates the same perspective view as FIG. 21A of the linkage subset 1000 with a transparent view of the return assembly 1002. FIG. 21C illustrates a front view of the linkage subset 1000 and a transparent view of the return assembly 1002. FIG. 21D illustrates a right side view of the linkage subset 1000 and the return assembly 1002. FIG. 21E illustrates a left side view of the linkage subset 1000 and the return assembly 1002. FIG. 21F illustrates a top view of the linkage subset 1000 and the return assembly 1002. FIG. 21G illustrates a bottom view of the linkage subset 1000 and the return assembly 1002.

The linkage subset 1000 is an example of the linkage subset 314 of the variable-length support assembly 306 described above with reference to FIG. 4 according to one embodiment of the present disclosure. The linkage subset 1000 comprises several individual linkages 1010 coupled to one another to form a portion of a variable-length support assembly akin to the variable-length support assembly 306 described above with relation to FIGS. 3 and 4. In the pictured embodiment, only the linkages 1010*a-e* are illustrated, although additional linkages may be present in the linkage subset 1000. Each of the linkages 1010 is substantially identical to one another, and the linkages 1010 include projections 1012 that are sized and shaped to interlock with each other. The shapes of the linkages 1010 and their projections 1012 should not be considered limiting features, as other shapes and configurations are contemplated for other embodiments of the present invention. These may include, for example, round, rectangular, oblong, elliptical, triangular, and square shapes.

Each linkage 1010 is coupled to an adjacent linkage 1010 by a bridging element 1015. For example, the linkages 1010*a* and 1010*b* are linked by the bridging element 1015*a*, the linkages 1010*b* and 1010*c* are linked together by the bridging element 1015*b*, and the linkages 1010*d* and 1010*e* are linked together by the bridging element 1015*c*. As shown in FIG. 20, the linkages 1010 are assembled in two opposite support members or strips 1020*a*, 1020*b* of linkages 1010 serially coupled by bridging elements 1015. The strips 1020*a*. 1020*b* define a central lumen 1025, as best illustrated in FIGS. which corresponds to the central lumen 315 described above with reference to FIG. 4.

The linkages 1010 of the two strips 1020*a*, 1020*b* are shaped and configured such that the linkages 1010 of one strip (e.g., the strip 1020*a*) can only engage with linkages 1010 of the opposite strip (e.g., the strip 1020*b*) when the projections 1012 are at an appropriate angle relative to one another. The projections 1012 of linkages 1010 from opposite strips 1020*a*, 1020*b* are shaped and sized to overlap and engage one another, thereby interlocking the strips 1020*a*, 1020*b* as the linkage subset 1000 assumes an expanded or "zipped up" configuration. The interaction of the projections 1012 prevents the two strips 1020*a*, 1020*b* from disengaging from one another along the expanded length of the variable-length support assembly. The linkages 1010 may be engaged or interlocked one at a time, in succession, as the linkages 1010 emerge from the return assembly 1002. Similarly, the strips 1020 may be "unzipped" and the linkages 1010 disengaged from one another as the linkages 1010 enter the return assembly 1002 and the linkage subset 1000 assumes a more compact or "unzipped" configuration.

Thus, the return assembly 1002 acts as a movable guide including two channels 130*a*, 1030*b* that are angled to guide the individual support members or linkage strips 1020*a*, 1020*b*, respectively apart from one another and through the return assembly 1002. As shown in FIG. 21B, the return assembly 1002 includes a central lumen 1032 that allows for the passage of a medical instrument such as, without limitation, a catheter. As the return assembly 1002 moves in the direction of the arrow A8 shown in FIG. 21C, the linkages 1010 nearest the return assembly 1002 encounter a guide element 1035 that nudges the strips 1020*a*, 1020*b* apart and into the separate channels 1030*a*, 1030*b*. The guide element 1035 is an angular central ridge or projection of the return assembly 1002. The linkages 1010 of different strips 1020*a*, 1020*b* separate from one another in succession, two at a time, in the direction of the arrow A8. The return assembly 1002 is configured such that by the passage of the return assembly 1002 in the direction of the arrow A8, the linkages 1010 of opposing strips 1020*a*, 1020*b* are drawn together and interlocked, while by the passage of the return assembly 1002 in the opposite direction (i.e., in the direction of an arrow A9), the linkages 1010 are disengaged and separated to enter the channels 1030a, 1030b.

Although the systems and methods of this disclosure have been described for use in the connected bronchial passageways of the lung, they are also suited for navigation and treatment of other tissues, via natural or surgically created connected passageways, in any of a variety of anatomical systems including the colon, the intestines, the kidneys, the brain, the heart, the circulatory system, or the like. The methods and embodiments of this disclosure are also suitable for non-interventional applications.

One or more elements in embodiments of the invention may be implemented in software to execute on a processor of a computer system such as control system 112. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. An apparatus for guiding an elongated flexible instrument, the apparatus comprising:
    a first plurality of linkages forming a first side of a channel of a variable-length support assembly;
    a second plurality of linkages forming a second side of the channel, opposite the first side;
    a third plurality of linkages disposed between the first and second plurality of linkages and forming a third side of the channel; and
    a fourth plurality of linkages disposed between the first and second plurality of linkages and forming a fourth side of the channel, opposite the third side;
    wherein each of the first, second, third, and fourth pluralities of linkages are separable from each other to transition the variable-length support assembly from an elongated configuration to a compact configuration.

2. The apparatus of claim 1, wherein the third plurality of linkages is interlocked with the first and second pluralities of linkages in the elongated configuration.

3. The apparatus of claim 2, wherein the fourth plurality of linkages is interlocked with the first and second pluralities of linkages in the elongated configuration.

4. The apparatus of claim 1, wherein advancement of the variable-length support assembly along a longitudinal axis defined through the channel causes an asynchronous unlocking of the first, second, third, and fourth pluralities of linkages from each other.

5. The apparatus of claim 4, wherein the variable-length support assembly is adapted to maintain a length of the elongated flexible instrument in a fixed configuration relative to the variable-length support assembly as the variable-length support assembly is moved along the longitudinal axis.

6. The apparatus of claim 1, wherein each pair of adjacent linkages of the first plurality of linkages is connected by a hinge component.

7. The apparatus of claim 6, wherein each linkage of the first plurality of linkages is configured for rotational movement about the hinge component relative to an adjacent linkage.

8. The apparatus of claim 1, wherein the linkages of each of the first, second, third, and fourth pluralities of linkages are connected to axially adjacent linkages in a linear formation.

9. The apparatus of claim 1, further comprising a return assembly configured to receive at least a portion of at least one of the first, second, third, or fourth pluralities of linkages to shorten the variable-length support assembly as the elongated flexible instrument and the variable-length support assembly are moved along a longitudinal axis of the variable-length support assembly.

10. The apparatus of claim 9, wherein the return assembly is configured to release at least some linkages of each of the first, second, third, and fourth pluralities of linkages to lengthen the variable-length support assembly as the elongated flexible instrument is moved along the longitudinal axis in a first direction.

11. The apparatus of claim 10, wherein advancement of the return assembly along the longitudinal axis in a second direction opposite the first direction separates a proximal end of the variable-length support assembly such that the third and fourth pluralities of linkages are separated from the first and second pluralities of linkages, directing each of the first, second, third, and fourth pluralities of linkages into the return assembly and causing the variable-length support assembly to assume the compact configuration.

12. The apparatus of claim 11, wherein directing each of the first, second, third, and fourth pluralities of linkages into the return assembly comprises rotating individual linkages of each plurality of linkages radially outward from the channel.

13. The apparatus of claim 11, wherein directing each of the first, second, third, and fourth pluralities of linkages into the return assembly comprises rotating individual linkages of each plurality of linkages about an axis transverse to the longitudinal axis.

14. The apparatus of claim 11, wherein separating a proximal end of the variable-length support assembly includes unlocking each linkage from circumferentially adjacent linkages by applying a force to each linkage to displace a flange of each linkage from a slot of an adjacent linkage.

15. The apparatus of claim 1, wherein each linkage is substantially identical to each other linkage.

16. The apparatus of claim 1, wherein when the variable-length support assembly is in the elongated configuration, a flange of a first linkage of the first plurality of linkages interlocks with a slot of a linkage of the third plurality of linkages, a flange of the linkage of the third plurality of linkages interlocks with a slot of a linkage of the second plurality of linkages, a flange of the linkage of the second plurality of linkages interlocks with a slot of a linkage of the fourth plurality of linkages, and a flange of the linkage of the fourth plurality of linkages interlocks with a slot of a second linkage of the first plurality of linkages.

17. The apparatus of claim 1, wherein when the variable-length support assembly is in the elongated configuration, a flange of a first linkage of the first plurality of linkages interlocks with a first slot of a linkage of the third plurality of linkages, and a flange of a second linkage of the first plurality of linkages interlocks with a second slot of the linkage of the third plurality of linkages.

18. The apparatus of claim 17, wherein when the variable-length support assembly is in the elongated configuration, a flange of the linkage of the third plurality of linkages interlocks with a slot of a linkage of the second plurality of linkages.

19. An apparatus for guiding an elongated flexible instrument, the apparatus comprising:
- a first plurality of linkages forming a first side of a channel of a variable-length support assembly;
- a second plurality of linkages forming a second side of the channel; and
- a third plurality of linkages disposed between the first and second plurality of linkages and forming a third side of the channel;
- wherein each of the first, second, and third pluralities of linkages are separable from each other to transition the variable-length support assembly from an elongated configuration to a compact configuration.

20. An apparatus for guiding an elongated flexible instrument, the apparatus comprising:
- a first plurality of linkages forming a first side of a channel of a variable-length support assembly, each linkage of the first plurality of linkages being pivotally coupled to an adjacent linkage of the first plurality of linkages when the variable-length support assembly is in an elongated configuration and when the variable-length support assembly is in a compact configuration;
- a second plurality of linkages forming a second side of the channel, each linkage of the second plurality of linkages being pivotally coupled to an adjacent linkage of the second plurality of linkages in the elongated configuration and in the compact configuration;
- a third plurality of linkages forming a third side of the channel, each linkage of the third plurality of linkages being pivotally coupled to an adjacent linkage of the third plurality of linkages in the elongated configuration and in the compact configuration; and
- a fourth plurality of linkages forming a fourth side of the channel, each linkage of the fourth plurality of linkages being pivotally coupled to an adjacent linkage of the fourth plurality of linkages in the elongated configuration and in the compact configuration;
- wherein, when the variable-length support assembly is in the elongated configuration, a first linkage of the first plurality of linkages is interlocked with a second linkage of the second plurality of linkages, the second linkage is interlocked with a third linkage of the third plurality of linkages, and the third linkage is interlocked with a fourth linkage of the fourth plurality of linkages; and
- wherein, when the variable-length support assembly is in the compact configuration, the first linkage is separated from the second linkage, the second linkage is separated from the third linkage, and the third linkage is separated from the fourth linkage.

* * * * *